United States Patent [19]
Simpson et al.

[11] Patent Number: 6,139,508
[45] Date of Patent: Oct. 31, 2000

[54] ARTICULATED MEDICAL DEVICE

[75] Inventors: Philip J. Simpson; David G. Matsuura, both of Escondido; John Kilcoyne, San Diego, all of Calif.

[73] Assignee: Endonetics, Inc., San Diego, Calif.

[21] Appl. No.: 09/248,361

[22] Filed: Feb. 10, 1999

Related U.S. Application Data

[63] Continuation-in-part of application No. 09/128,882, Aug. 4, 1998.

[51] Int. Cl.[7] .................................... A61B 10/00
[52] U.S. Cl. ......................... 600/564; 600/567; 606/167; 606/205; 606/207
[58] Field of Search ..................... 600/562, 564, 600/567; 606/52, 167, 170, 171, 174, 175, 205, 206, 207, 208, 209

[56] References Cited

U.S. PATENT DOCUMENTS

| | | | |
|---|---|---|---|
| 4,174,715 | 11/1979 | Hasson | 128/321 |
| 4,243,048 | 1/1981 | Griffin | 128/751 |
| 4,640,296 | 2/1987 | Schnepp-Pesch et al. | 128/754 |
| 4,887,612 | 12/1989 | Esser et al. | 128/751 |
| 5,052,402 | 10/1991 | Bencini et al. | 128/751 |
| 5,172,700 | 12/1992 | Bencini et al. | 128/751 |
| 5,195,533 | 3/1993 | Chin et al. | 128/754 |
| 5,251,641 | 10/1993 | Xavier | 128/754 |
| 5,320,627 | 6/1994 | Sorensen et al. | 606/167 |
| 5,373,854 | 12/1994 | Kolozsi | 128/749 |
| 5,385,570 | 1/1995 | Chin et al. | 606/170 |
| 5,415,182 | 5/1995 | Chin et al. | 128/754 |
| 5,538,008 | 7/1996 | Crowe | 128/751 |
| 5,542,432 | 8/1996 | Slater et al. | 128/751 |
| 5,562,102 | 10/1996 | Taylor | 128/751 |
| 5,573,008 | 11/1996 | Robinson et al. | 128/754 |
| 5,573,546 | 11/1996 | Nakao | 606/205 |
| 5,620,459 | 4/1997 | Lichtman | 606/174 |
| 5,638,827 | 6/1997 | Palmer et al. | 600/564 |
| 5,647,115 | 7/1997 | Slater et al. | 29/557 |
| 5,665,100 | 9/1997 | Yoon | 606/170 |
| 5,709,697 | 1/1998 | Ratcliff et al. | 606/167 |
| 5,762,069 | 6/1998 | Kelleher et al. | 128/751 |
| 5,776,075 | 7/1998 | Palmer | 600/564 |
| 5,797,957 | 8/1998 | Palmer et al. | 606/167 |
| 5,820,630 | 10/1998 | Lind | 606/208 |
| 5,843,000 | 10/1998 | Nishioka et al. | 600/566 |
| 5,871,453 | 2/1999 | Banik et al. | 600/564 |
| 5,895,361 | 4/1999 | Turturro | 600/562 |
| 5,919,202 | 7/1999 | Yoon | 606/170 |
| 5,922,002 | 7/1999 | Yoon | 606/170 |

FOREIGN PATENT DOCUMENTS

| | | |
|---|---|---|
| 2 479 680 | 4/1980 | France . |
| 1629038 A1 | 5/1988 | U.S.S.R. . |

*Primary Examiner*—Cary O'Connor
*Assistant Examiner*—Charles Marmor, II
*Attorney, Agent, or Firm*—Knobbe, Martens, Olsen and Bear, LLP

[57] ABSTRACT

An articulated medical device as disclosed, incorporated in one embodiment into a biopsy device. The biopsy embodiment comprises an elongated actuator shaft which is slidable within an outer sleeve. A jaw portion coupled to the actuator shaft and the outer sleeve opens when the shaft is moved in a first direction relative to the sleeve and closes when the shaft is moved in a second direction relative to the sleeve.

43 Claims, 24 Drawing Sheets

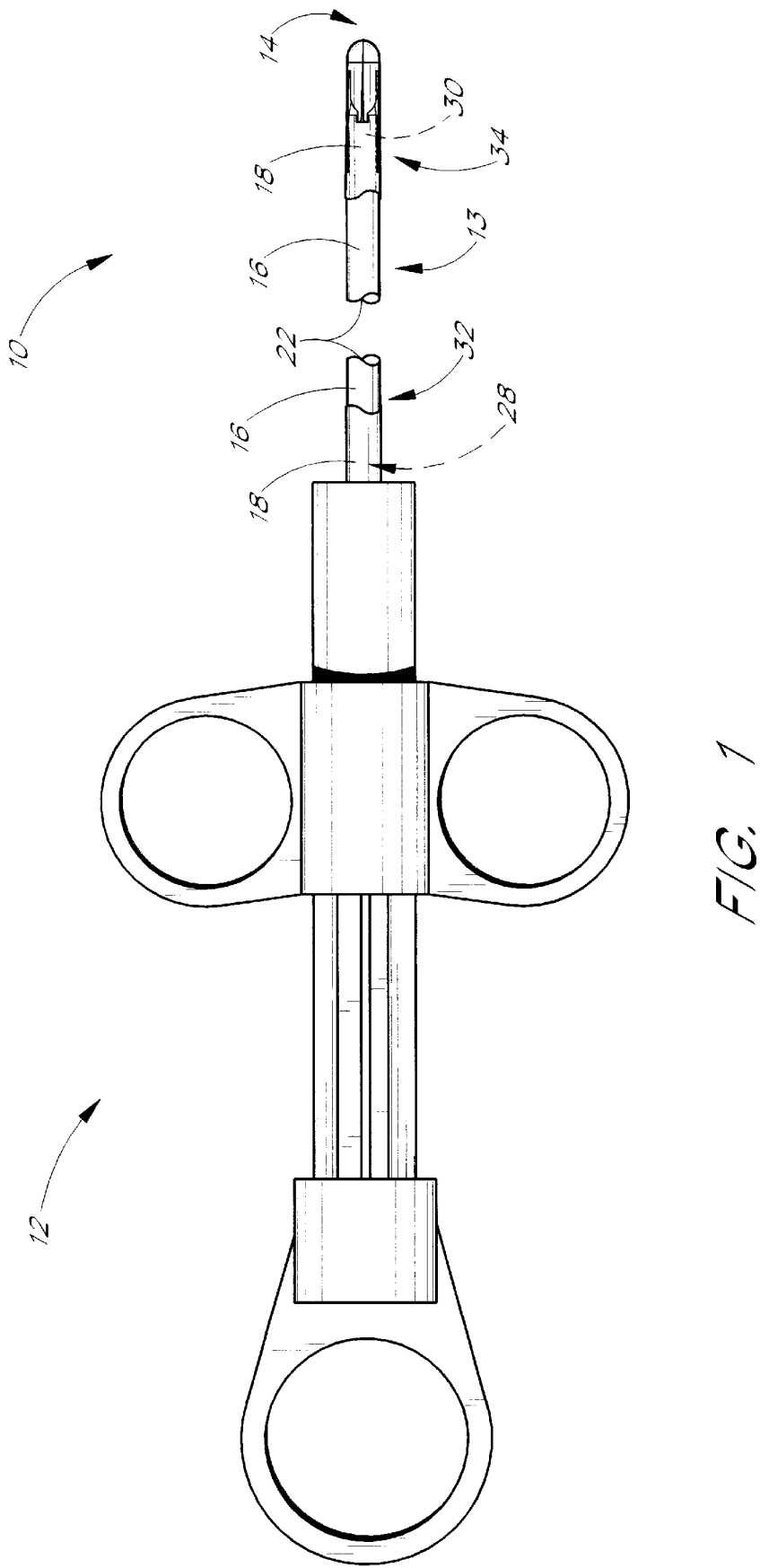

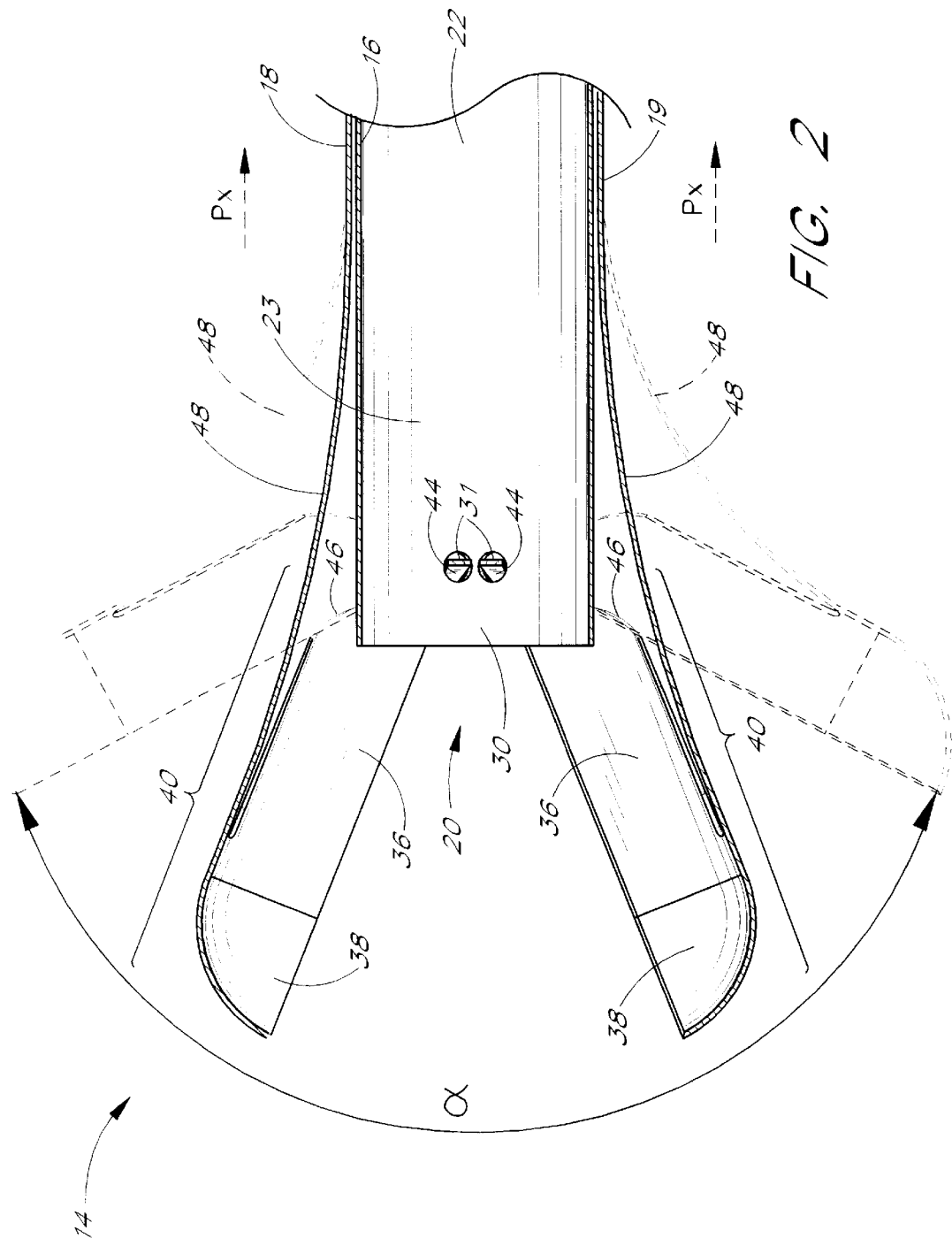

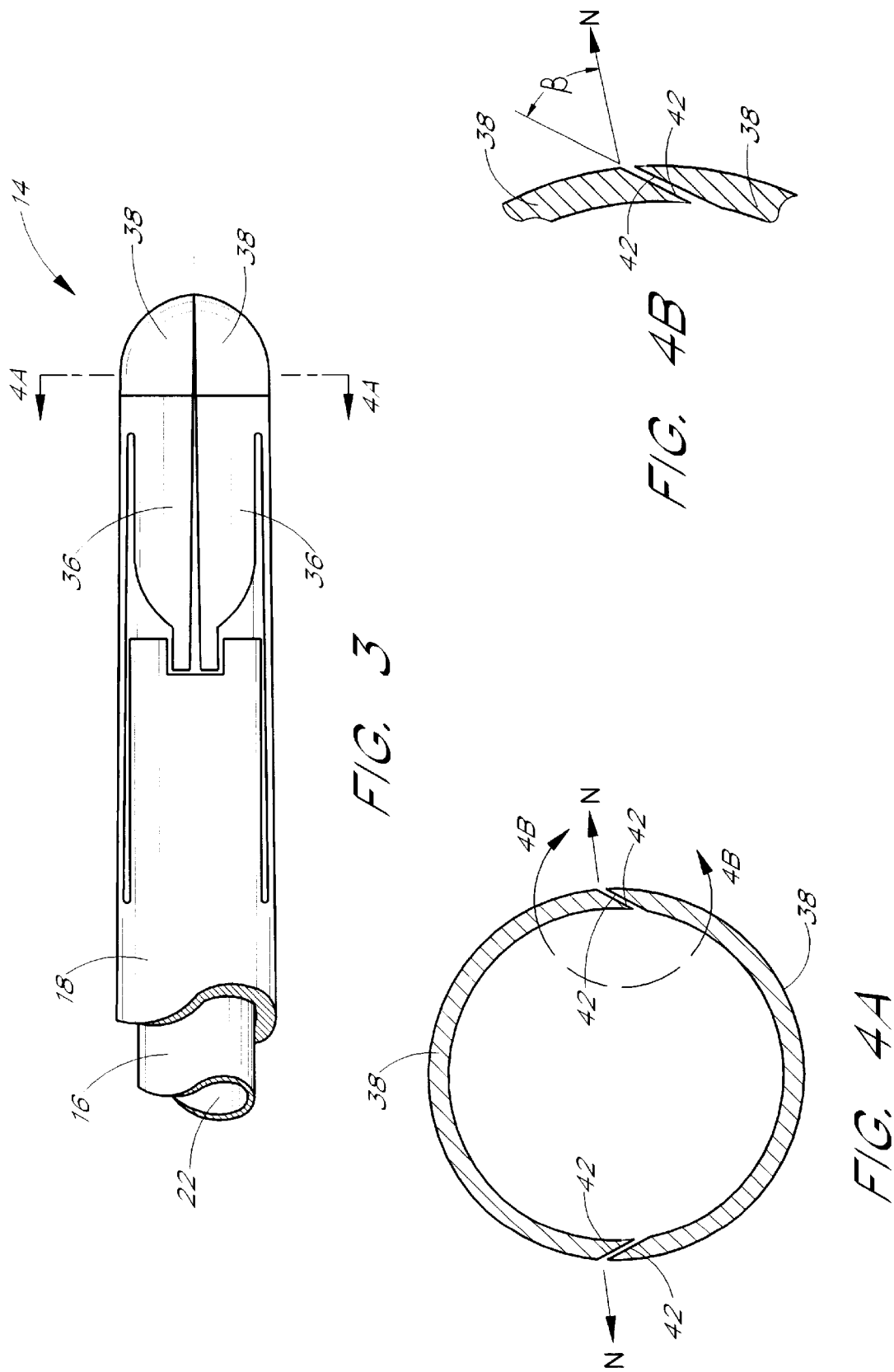

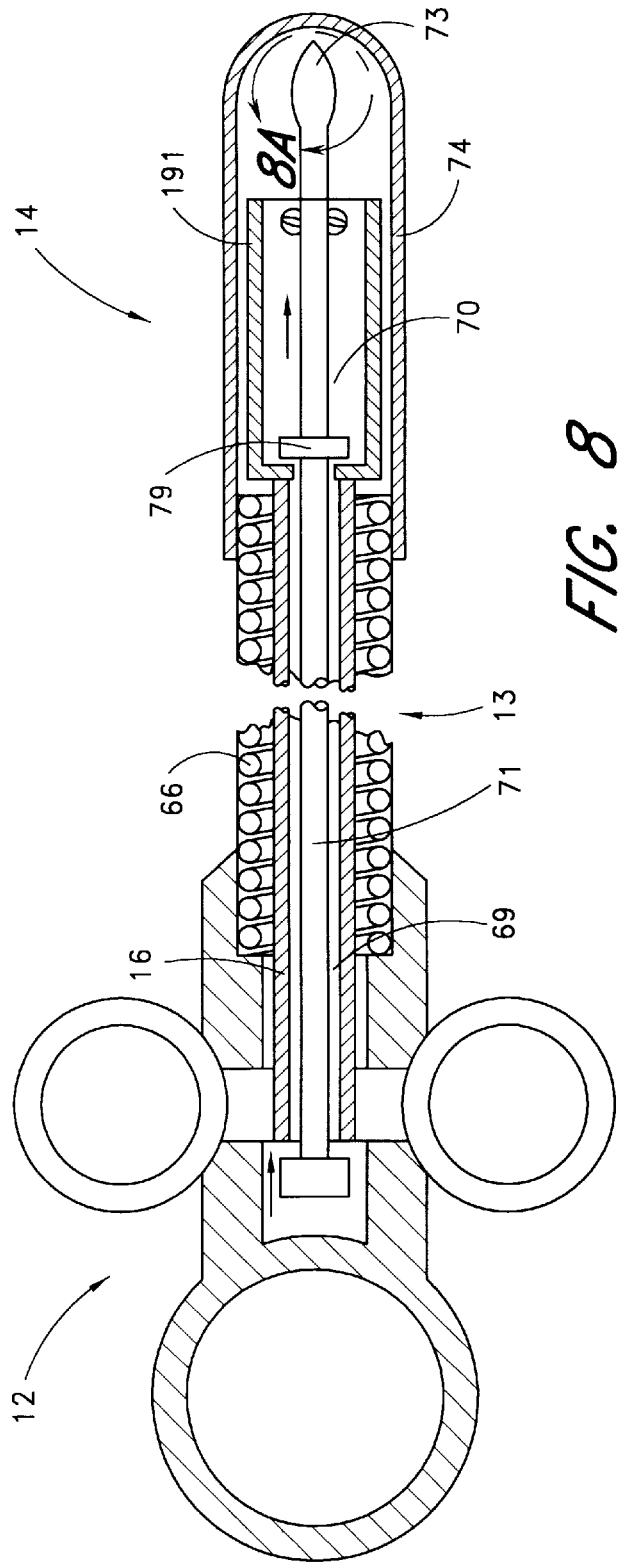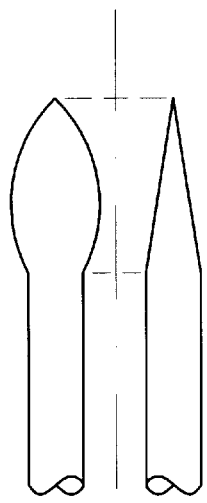

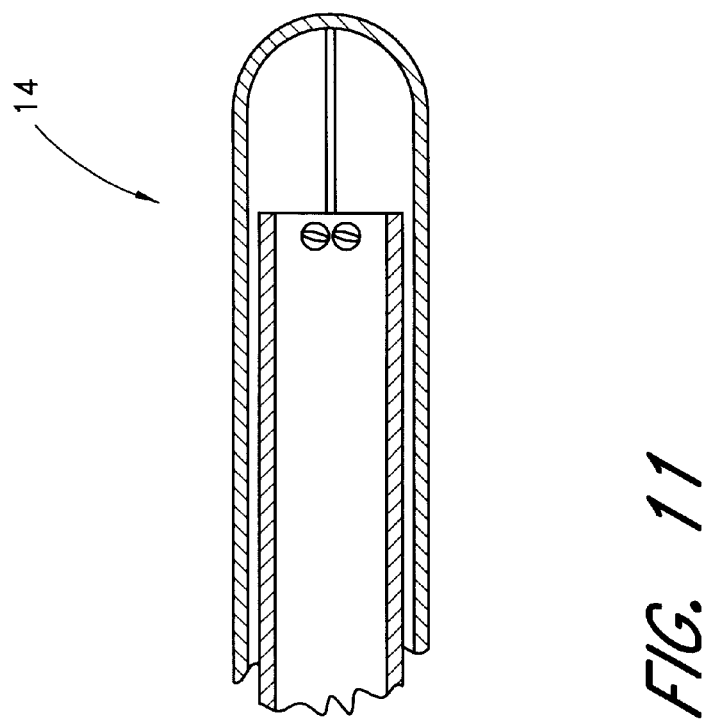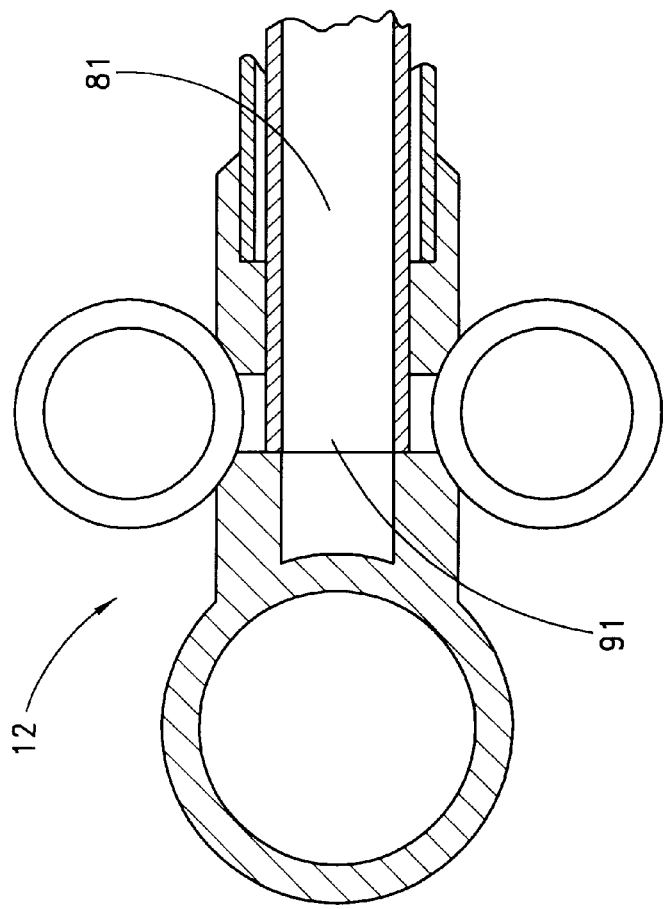
FIG. 11

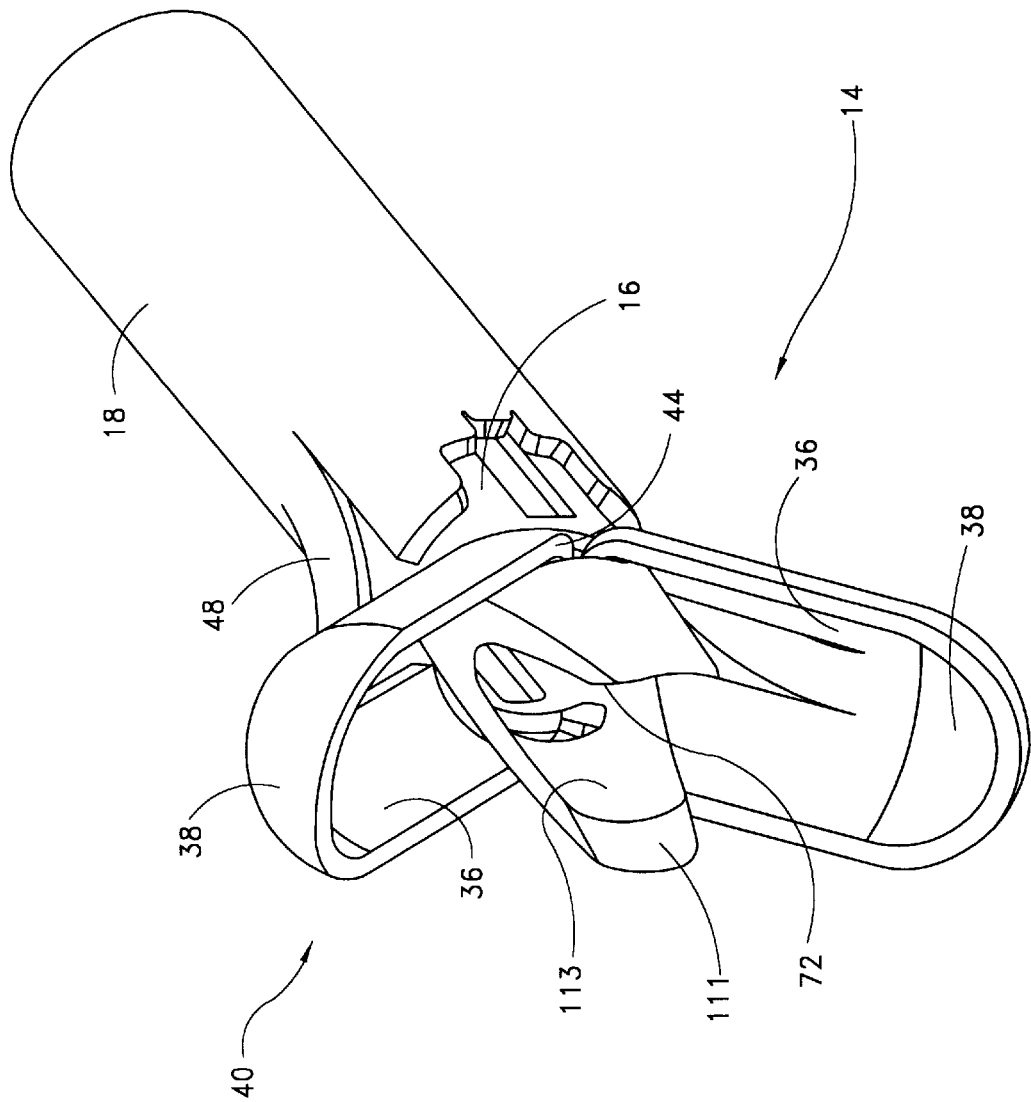

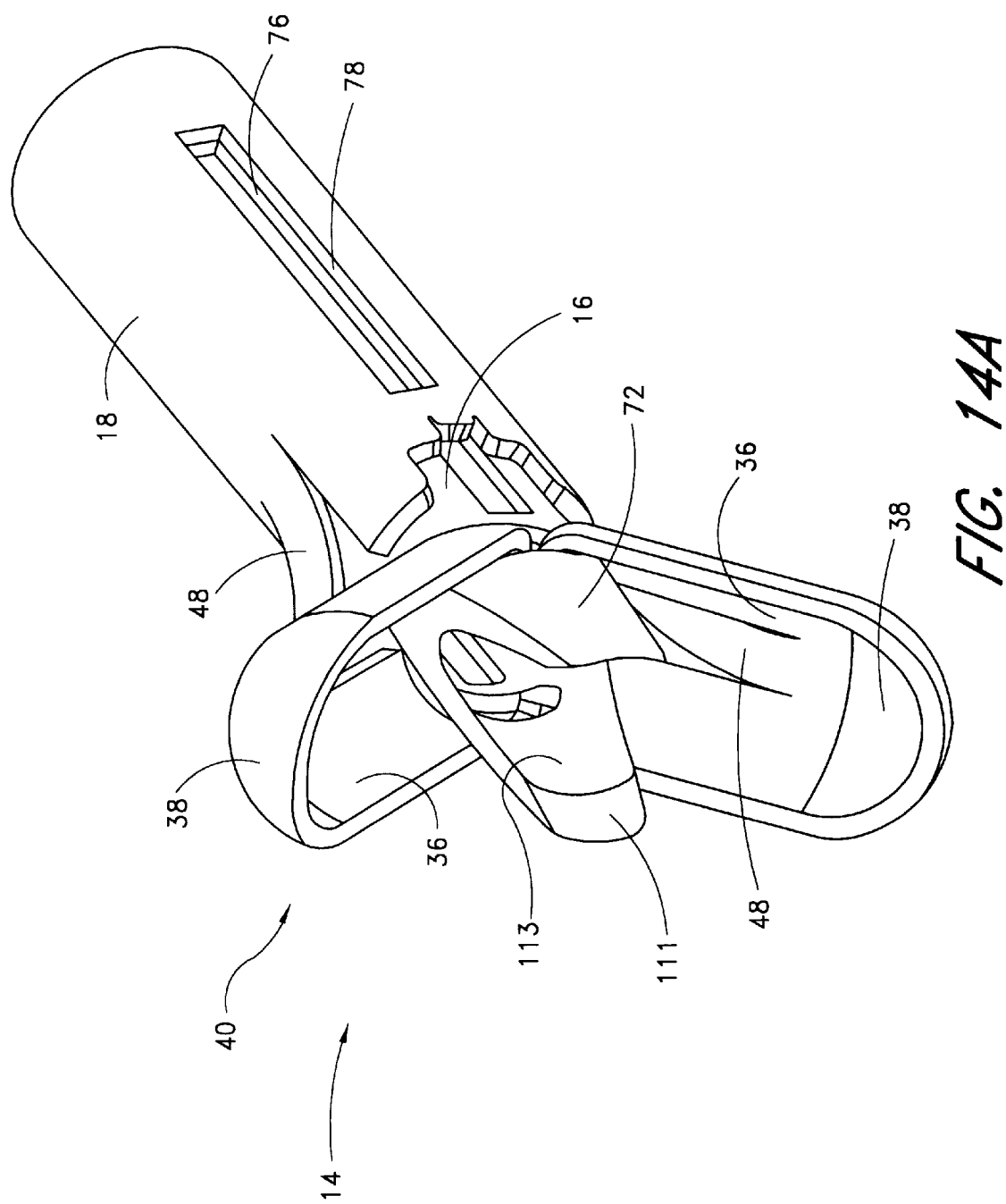

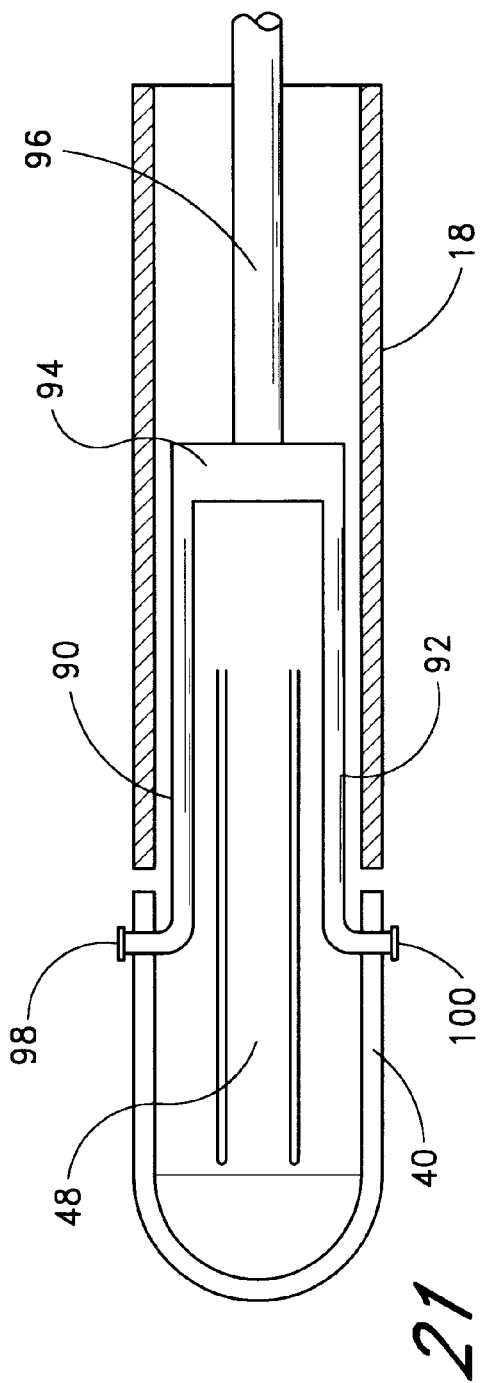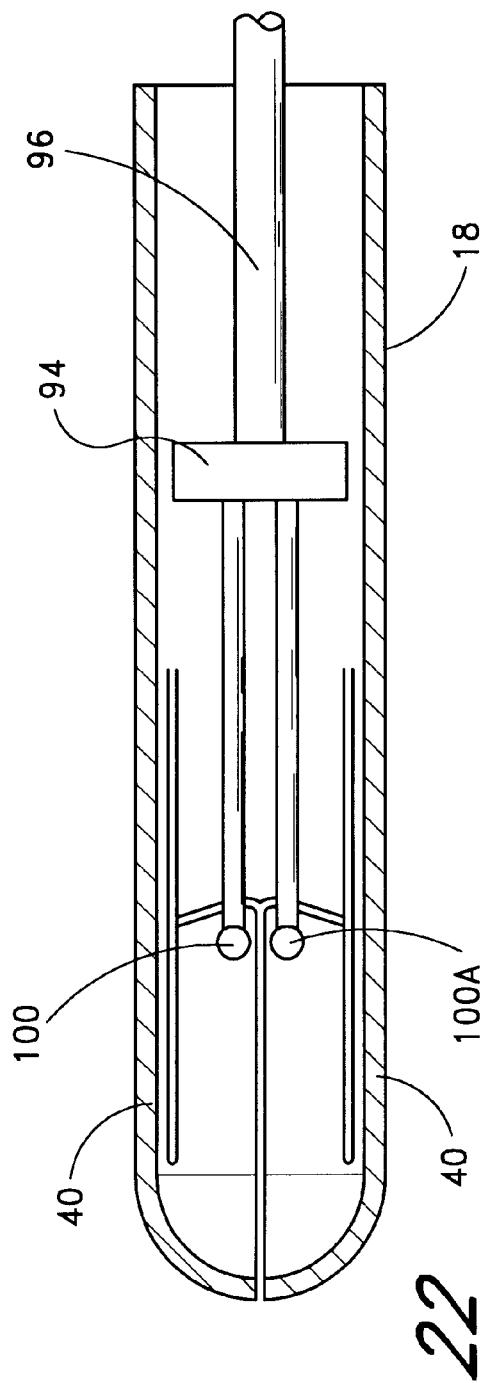

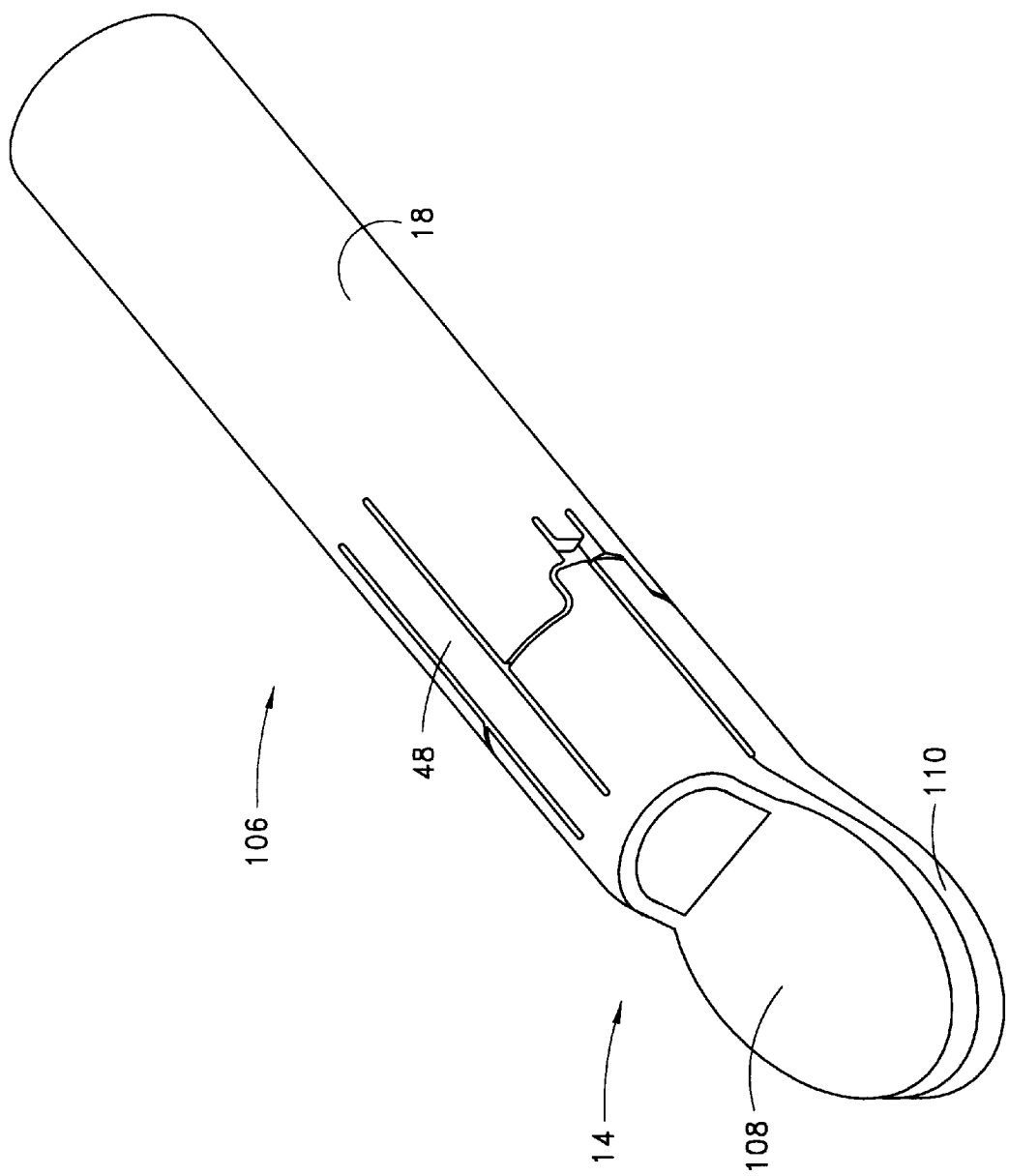

ARTICULATED MEDICAL DEVICE

The present application is a continuation-in-part of application Ser. No. 09/128,882 filed on Aug. 4, 1998, entitled Multiple Sample Biopsy Device.

BACKGROUND OF THE INVENTION

The present invention relates to medical instruments. More particularly, the present invention relates to an articulated mechanism useful in devices such as forceps, single or multiple sample biopsy devices, articulated electrodes and the like.

Devices for the retrieval of tissue samples from within a patient are frequently used in conjunction with instruments such as flexible endoscopes. Endoscopes allow the visualization of internal structures of a patient by a clinician without the need for conventional exploratory surgery. When suspicious lesions or tissue masses are encountered during an endoscopic examination, it is helpful to excise and remove a small sample of the tissue for further analysis by a pathology laboratory.

Flexible biopsy forceps are often used to perform such tissue excision and retrieval. Conventional biopsy forceps may consist of an elongated, tightly-wound spring-coil body. The spring body has a control assembly at a proximal end and a jaw assembly at a distal end. The control assembly is typically a hand-operated push-pull mechanism that slides a control wire back and forth through a lumen of the spring-coil body. The control wire is usually attached to a pair of pivoting jaws in the jaw assembly. Pushing and pulling on the control wire opens and closes the jaws, respectively. Moreover, the jaws are typically joined to the body through a pivot pin which spans at least a portion of the lumen. Thus, the lumen is typically at least partially blocked or occluded by mechanical elements.

When used with a flexible endoscope, the forceps are inserted into the working channel of the endoscope and advanced distally. The tip of the endoscope is directed by the clinician using controls on the proximal end of the endoscope. Once the target site has been identified and is under direct vision, the forceps are advanced distally out of the working channel and the jaws are opened. Upon contact with the tissue, the jaws are tightly closed and the forceps are retracted slightly to cut and remove the tissue sample. Flexible biopsy forceps can also be used without an endoscope, as in, for instance, cardiac muscle biopsy procedures. In such procedures, the flexible biopsy forceps device is inserted through a blood vessel into a heart chamber, where a sample of cardiac tissue is excised.

With certain types of endoscopic examinations, it is necessary to take more than one tissue sample. For example, in surveying a region of a bowel for specific disease states, it is sometimes necessary to take between ten and twenty tissue samples. In these instances, the use of conventional biopsy forceps is time-consuming because the forceps must be withdrawn and re-inserted after each sample has been excised. Maintaining the tip of the endoscope in a steady position during the removal and re-insertion of the forceps is often a tedious and difficult task. Accordingly, the clinician's ability to keep track of which areas have been biopsied and which have not can be impaired. The impairment of this ability can result in a frustrating and lengthy procedure for both the patient and clinician.

There is, therefore, a need for a biopsy device capable of retrieving more than one tissue sample from within a patient. It is also preferable for the collected samples to be of a size comparable to those obtained from conventional biopsy forceps devices, and for such samples to be easily removed from the device. Moreover, it is desirable for the samples to be held in the order of collection for identification of the source of each sample. It is further desirable for such a device to be relatively inexpensive and easy to use. In addition, a variety of other instruments such as graspers, spreaders, electrodes, single sample biopsy devices and the like would benefit from a single low profile articulating mechanism such as that disclosed herein.

SUMMARY OF THE INVENTION

There is provided in accordance with one aspect of the present invention an articulating mechanism for use in a medical device. The articulating mechanism comprises a tube, and an actuator, axially moveably positioned within the tube. At least one laterally pivotable element is provided, at least a portion of which is integrally connected to the tube. Axial movement of the actuator with respect to the tube causes lateral movement of the pivotable element. In one embodiment, two laterally pivotable elements are provided. The integral connection between the laterally pivotable element and the tube preferably comprises at least one flexure member. Preferably, each laterally pivotable element is provided at its distal end with an operative element such that the medical device can function as a biopsy device, forcep, electrode, grasper, cutter, dilator, expander or dissector.

There is provided in accordance with another aspect of the present invention an articulated medical device in the form of a tissue collection device. The device comprises an elongate body, having a proximal end and a distal end. A control is provided on the proximal end. A cutter tip is provided on the distal end, the tip comprising first and second opposing jaws and at least one distally extending sample guide prong in the cutting tip. The body may comprise either a flexible tubular body or a relatively rigid tubular body. In one embodiment, the body comprises an elongate outer tube having an axially reciprocally moveable inner actuator tube therein. Proximal or distal motion of the actuator tube relative to the outer tube operates the cutting tip. In a further embodiment, the elongate tubular body is provided with a sample ejector, such as an axially elongated aperture on the side wall of the tubular body to permit introduction of a sample ejection device.

In accordance with another aspect of the present invention, there is provided a method of obtaining one or more tissue samples. The method comprises the steps of providing a sample collection device, having a sample collection chamber for receiving multiple tissue samples. The device has a pair of opposing jaws for isolating the samples from surrounding tissue, and at least one distally extending sample guide prong. The device is introduced into the body and a first tissue sample is guided along the tissue guide prong and into the jaws. The jaws are thereafter closed to isolate the first tissue sample. A second tissue sample is thereafter advanced along the tissue guide prong and into the jaws, and the jaws are thereafter closed to isolate the second tissue sample.

In accordance with a further aspect of the present invention, there is provided a cutter tip for mounting on the distal end of a biopsy device. The tip comprises a tubular housing having a proximal end and a closeable distal end, the distal end axially bisected into first and second jaw portions by a proximally extending cut therethrough. At least one sample guide prong extends distally within the first and second jaws, and a tubular sample collection container is axially moveably positioned within the housing. A moveable connection between the tubular sample container and the first and second jaws causes axial displacement of the tubular sample container in a first direction to move the first and second jaws laterally away from each other and axial displacement of the tubular sample container in a second axial direction causes the first and second jaws to advance medially towards each other.

In one embodiment, each of the first and second jaws is provided with at least one flexural element extending between the tubular housing and the jaw. In another embodiment, each jaw is provided with two flexural elements. The flexural member or members may be intregally formed with the jaw and the tubular housing. In one embodiment, the sample guide prong is an integral extension of the wall of the sample container.

Further features and advantages of the present invention will become apparent to those of skill in the art in view of the detailed description of preferred embodiments which follows, when considered together with the attached drawings and claims.

BRIEF DESCRIPTION OF THE DRAWINGS

These and other features, aspects and advantages of the present invention will now be described with reference to the drawings of several currently preferred embodiments which are intended to illustrate and not to limit the present invention, and in which:

FIG. 1 is a side elevational view of an embodiment of a multiple sample biopsy device attached to an exemplary actuating handle;

FIG. 2 is an enlarged cross-sectional side elevational view of the distal tip of the embodiment of FIG. 1 with a fully opened pair of jaws illustrated in phantom;

FIG. 3 is an enlarged side elevational view of the distal tip of the embodiment of FIG. 1;

FIG. 4A is a cross section through FIG. 3 taken along line 4A—4A;

FIG. 4B is an enlarged view of the area within line 4B—4B in FIG. 4A;

FIG. 8 is a cross-sectional side elevational view of a flexible shaft embodiment of the present invention, having a central lumen for auxiliary functions.

FIG. 11 is a cross-sectional side elevational view of a rigid shaft embodiment of the present invention.

FIG. 14 is a front perspective view of a cutting tip having distally extending sample guide prongs.

FIG. 14A is a front perspective view as in FIG. 14, additionally illustrating a sample ejection slot.

FIG. 21 is a cross sectional view of an alternate embodiment of the present invention.

FIG. 22 is a cross section of the device of FIG. 21, rotated 90° about its longitudinal axis.

FIG. 25 is a perspective view of a distal tip in accordance with the present invention, adapted for use as graspers, dilators, expanders, dissectors or the like.

DETAILED DESCRIPTION OF THE PREFERRED EMBODIMENTS

Figure 5A:
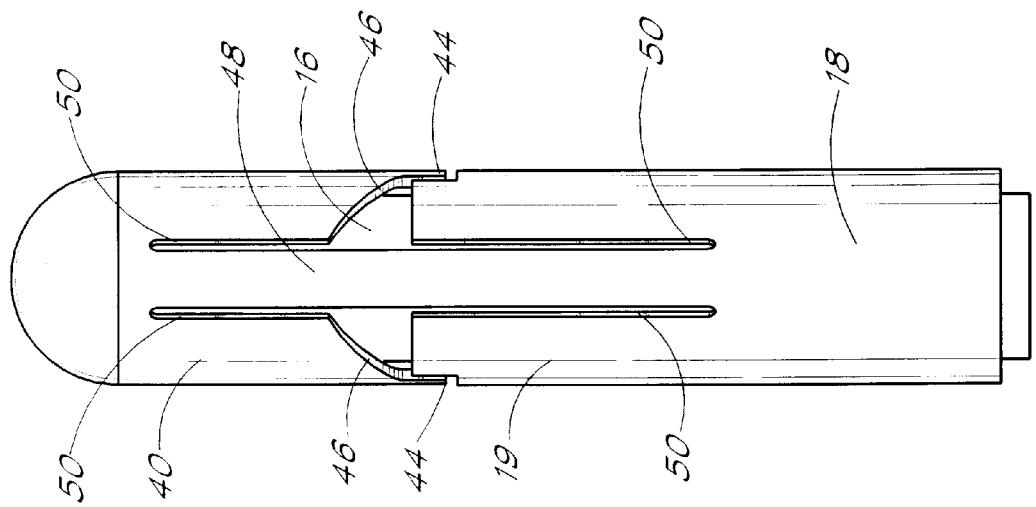
FIG. 5A is a top plan view of the distal tip of the embodiment of FIG. 1, illustrating a stopping edge and a straight-edged flexure member.
Figure 6:
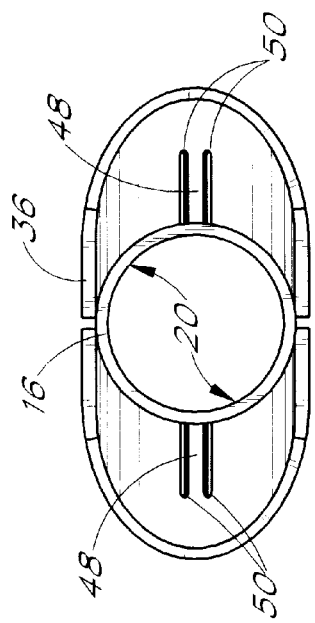
FIG. 6 is an end view of the embodiment of FIG. 1 with the hemispherical cap portions removed and the jaw members in an open position.
Figure 5B:
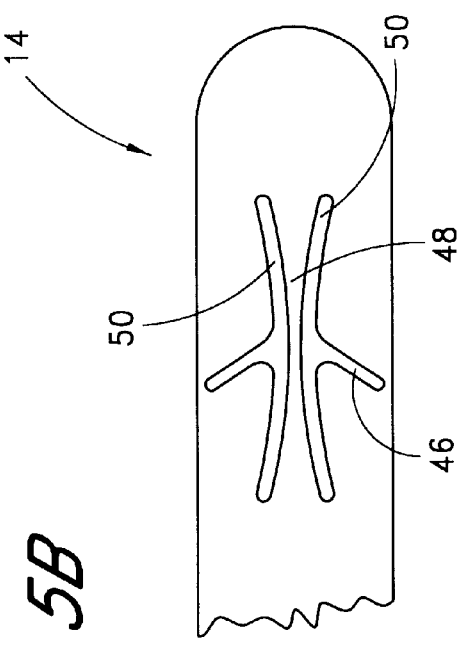
FIGS. 5B–5F are top plan views of additional embodiments of the cutting tip modified to reduce or redistribute stress in and around the flexure member.

Referring to FIG. 1, there is illustrated a single or multiple sample biopsy device 10 configured in accordance with certain aspects of the present invention. In general, the biopsy device 10 comprises a proximal control or handle 12, an elongate body portion 13 and a cutting tip 14. As will be apparent to those of skill in the art in view of the disclosure herein, the cutting tip 14 of the present invention can readily be adapted for attachment to either a relatively rigid or relatively flexible body 13, of varying lengths and diameters, depending upon the desired clinical application.

For example, the concentric tubular structure disclosed in FIG. 1 will inherently produce a relatively rigid body which may be useful for laparoscopic, arthroscopic or other linear access applications as will be apparent to those of skill in the art.

Alternatively, the flexible body illustrated in FIGS. 7–10 may be used in conjunction with bronchoscopes, gastroscopes, sigmoidoscopes, colonoscopes, duodenoscopes, and other flexible introducer sheaths and equipment which are well known in the art. The flexible shaft embodiments are thus useful for advancement through any of a variety of tortuous pathways, including the GI tract, airways, and cardiovascular system, among other applications. Optimization of the cutting tip 14 of the present invention together with its flexible or rigid body 13 for any particular application can be readily accomplished by those of skill in the art in view of the disclosure herein.

As will become evident, the handle 12 used with the single or multiple sample biopsy device of the present invention need only move a first actuating element relative to a second actuating element to control the operation of a distal cutting tip on the device. The particular handle 12 illustrated herein is considered exemplary, and any of a wide variety of handle designs can be used. Further discussion of the handle is thus considered unnecessary.

Handle 12 (FIG. 1) is operatively linked to one or more cutting edges on the cutting tip 14, by way of a first actuating element such as actuator shaft 16, axially movably disposed with respect to a second actuating element such as an outer sleeve 18. Axial movement of the actuator shaft 16 in a first direction within the sleeve 18 closes cutting jaws on the cutting tip, allowing a sample of tissue to be severed from the patient and deposited within the jaws or collection chamber. Movement of the actuator shaft 16 in an opposite direction relative to the outer sleeve 18 in the illustrated configuration opens the jaws to allow the jaws to be advanced or otherwise repositioned to obtain a subsequent sample. Accordingly, the jaws open and close through a positive application of force and do not close purely as a result of a spring force or other biasing force.

With reference to FIGS. 1–3, the illustrated actuator shaft 16 useful for rigid body embodiments will be described in detail. In one embodiment used for laparoscopic procedures such as biopsies of the ovaries or uterus, the shaft 16 is a thin-wall metal tube having an outside diameter of between about 1.5 mm and about 5 mm. In general, the wall thickness of the outer sleeve 18 is chosen to optimize column strength and inside diameter while maintaining an acceptable O.D. for the desired procedure. Wall thicknesses generally within the range of from about 0.005" to about 0.020" may be used in a stainless steel construction.

Because the actuator shaft 16 extends from the control portion 12 (FIG. 1) to near the distal extremity of the device 10, the actuator shaft length varies according to its application. In general, the actuator shaft length can range from about 15 cm or less to about 50 cm or more depending upon the application. Any of the foregoing dimensions can be readily varied by persons of skill in the art, depending upon the intended use and performance characteristics of the device.

Although the actuator shaft 16 is illustrated in FIG. 1 as a tubular element, a solid rod having a round, rectangular or other cross-section may also be used. Alternative structures such as a spring coil tubular element may also be used, particularly in an embodiment in which the push/pull relationship between the shaft 16 and outer sleeve 18 are reversed from the illustrated embodiment so that cutting action is achieved by a distal, compressive force on the shaft 16. Polymeric materials may also be used, such as solid rods or extruded tubular elements, using any of a wide variety of relatively rigid plastics well known in the medical device field. In general, the first actuator such as actuator shaft 16 must simply have sufficient column strength and/or pulling strength to transmit sufficient axial force to the distal cutting tip to accomplish the clinical objectives of the biopsy tool.

In either the rigid shaft embodiments or the flexible shaft embodiments, discussed below, the actuator shaft 16 may be a solid structure, or be provided with a central lumen such as to permit the passage of biopsy samples in a proximal direction, or to accommodate additional implements or tools such as visualization and/or illumination devices, as discussed elsewhere herein. In addition, the central lumen in a hollow actuator shaft 16 may be utilized to permit passage of the device over a guidewire, such as in central or peripheral coronary vascular applications, or to permit infusion of fluids with or without medication, or to permit the aspiration of fluid or other samples.

The proximal portion 28 of the actuator shaft 16 is coupled to the control 12 to allow the clinician to control the desired axial translation of the actuator shaft 16 relative to the outer sleeve 18. In the illustrated embodiment, the actuator shaft 16 is coupled to the handle through a type of tensile-compressive connection (not shown). Any of a wide variety of joining techniques, such as mechanical interfit, pins, screws, solvent or adhesive bonding, heat welding and the like, depending upon the construction materials, can be used at both the proximal and distal ends of the actuator shaft 16. Because the actuator shaft is connected to the handle portion in any suitable manner, further discussion of the connecting structure is considered unnecessary.

Figure 13:
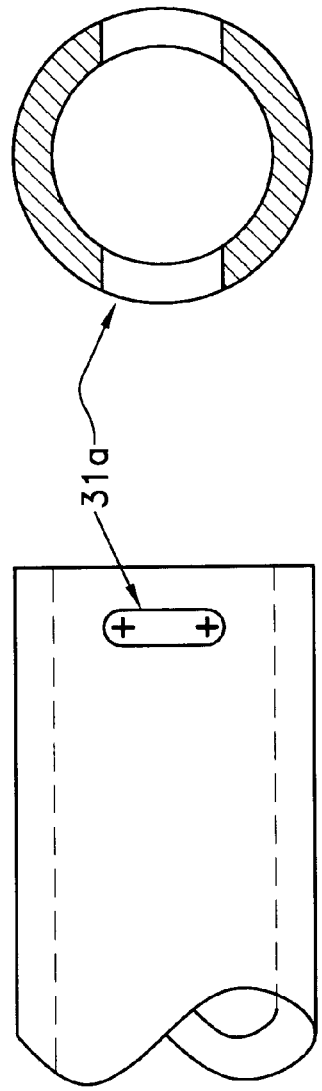
FIG. 13 is an alternate embodiment of the detail view shown in FIG. 12.

As shown in FIG. 2, the distal portion 30 of the illustrated actuator shaft 16 is provided with a plurality of jaw mounting apertures 31. In the illustrated embodiment, two pair, or a total of four, mounting apertures 31 are provided. Alternatively, circumferentially extending slots (see FIG. 13) may be used. The illustrated jaw mounting apertures 31 are longitudinally aligned and arranged in pairs to permit pivotal attachment of each jaw member.

Although the mounting apertures 31 are illustrated as extending through the inner actuator shaft 16, for receiving radially inwardly extending tabs from the outer sleeve 18, any of a variety of alternative structures can be utilized to accomplish the hinging function for cutting tip 14. For example, hinge pins or projections can extend radially outwardly from the actuator shaft 16, through corresponding apertures in the outer sleeve 18. Alternatively, any of a variety of flexible or pivotable hinge structures can be adapted for use in the present context, as will be apparent to those of skill in the art in view of the disclosure herein. In addition, although the hinge apertures 31 described above extend through a distal portion 30 of the actuator shaft 16, analogous hinge mounting apertures will extend through the housing of a sample collection container in flexible shaft embodiments such as those illustrated in FIGS. 7–10 where the actuator shaft is provided with a separate sample collection container at its distal end.

As shown in FIG. 1, the outer sleeve 18, which cooperates with the actuator shaft 16 to allow the manipulation of the cutting tip 14 also has a proximal portion 32 and a distal portion 34. In one embodiment used for procedures such as esophageal biopsy, the sleeve 18 is a thin-wall metal tube having an outside diameter of between about 0.090" and about 0.125". The inside diameter provides sufficient clearance for a sliding fit with the actuator shaft 16 in the rigid shaft embodiment. The sleeve 18 also has a wall thickness between about 0.005" and about 0.010".

The outer sleeve 18 also extends from the control portion 12 to nearly the distal extremity of the device 10. Accordingly, the outer sleeve length varies according to its application.

In one embodiment, the proximal portion 32 of the outer sleeve 18 desirably extends to the handle portion 12 and is coupled thereto such that the inner actuator shaft 16 can translate therein. The distal portion 34 extends substantially to the proximal extremity of the cutting tip 14 in some embodiments. In the embodiment illustrated in FIG. 1, the jaw portions of cutting tip 14 are integrally formed with the outer sleeve 18.

With reference now to FIG. 2, the tip 14 of the biopsy device 10 will be described in detail. As illustrated, in one embodiment, the tip 14 has two or more jaws 40 each of which comprises a partial cylindrical portion 36 which is combined with a corresponding partial spherical cap portion 38 at its distal extremity. The jaw members 40 in a two jaw embodiment may be manufactured by forming a hemispherical cap 38 on the distal extremity of the cylindrical outer sleeve 18 or short cylindrical segment in a flexible shaft embodiment. The hemispherical cap and cylindrical sleeve are then axially bisected by laser cutting or any of a variety of other conventional cutting techniques. Alternatively, the cap can be formed, soldered, bonded, brazed, or welded in any suitable manner to affix it to the distal extremity of outer sleeve 18. Additionally, where the outer sleeve 18 is molded or extruded of a suitable polymer, the cap 38 can be formed unitarily with or thermally bonded, soldered, solvent or adhesive bonded, etc. to the balance of the outer sleeve 18.

As further illustrated in FIGS. 4a and 4b, the illustrated first and second jaw members 40 are provided with mating cutting edges 42. To form the complementary pair of cutting edges 42, an axially extending cut is made through both side walls of the cutting tip 14 from the distal end (i.e., through the cap 38). The longitudinal cut extends proximally for a desired distance. In the illustrated embodiment, the longitudinal cut extends from the distal extremity (i.e., the cap 38) for approximately the axial length of the jaw 40. In general, the jaw 40 can vary in axial length from about 0.1" to about 0.2" in the preferred endoscopic device disclosed herein. However, jaw lengths of as much as about 0.75" or greater can be used for larger diameter tools, as will be apparent to those of skill in the art.

As illustrated in FIGS. 4A and 4B, the cut in the illustrated embodiment is skewed relative to normal, N, by an angle β, through at least the cap 38 of the jaw portion 14. By skewing the cut, two complimentary tissue biting edges are formed. In one embodiment, the cut is skewed between about 40° and about 50° from normal. The cutting edges 42 help to reduce the compressive force necessary to cut through the tissue sample to ease the removal of the sample from the patient. As will be recognized by those of skill in the art, the edges may also be bluntly formed such as by a normal cut relative to the surface of the hemispherical portion or the cylindrical sidewalls. Serrations or multiple cutting teeth (e.g. FIG. 24) may alternatively be provided.

As best shown in FIG. 2, the proximal end of each jaw member 40 has a pair of inwardly extending, substantially opposing mounting tabs 44. The tabs 44 act as pivot points in the holes 31 located in the actuator shaft 16. Accordingly, the linear distance between the distal extremity of the jaw members 40 and the tabs 44 define the radius for the arc of travel for each jaw member when opening and closing. In an embodiment designed for procedures such as esophageal, colonic or gastric biopsy, the distance is generally between about 0.150" and about 0.170".

In the illustrated embodiment, the mounting tabs 44 are aligned with a corresponding pair of jaw mounting apertures 31. By positioning these tabs 44 on opposing sides of each jaw member 40, the jaw member 40 may be securely pivotably mounted to the remainder of the biopsy device. The length of each tab 44 in the radial direction is generally not substantially greater than the wall thickness of the actuator shaft 16, so that the sample collection chamber (central lumen) in the distal portion of the device remains substantially unobstructed.

Figure 12:
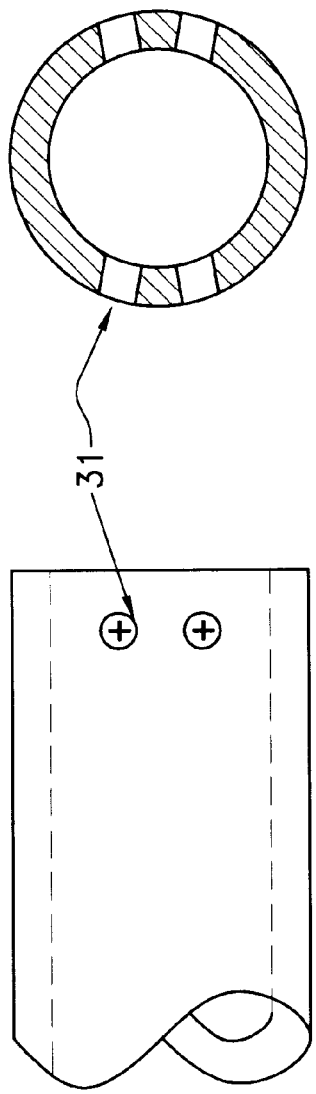
FIG. 12 is a detail view of the distal end of the inner actuating sleeve or collection chamber.

The circumferential orientation of the apertures 31 in FIG. 2 is illustrated in further detail in FIG. 12. In the illustrated embodiment, the opposing pair of apertures 31 for any given jaw 40 are separated from each other by about 160°. Thus, the opposing aperture pair 31 for any given jaw 40 are positioned at approximately 10° off of the part line between the two opposing jaws. An equivalent function can be accomplished by provided a circumferentially extending slot such as slot 31A illustrated in FIG. 13. In the illustrated embodiment, the long axis of the slot has a length on the order of about 0.024 inches. Other specific hinge arrangements can be readily determined by persons of ordinary skill in the art in view of the disclosure herein.

With reference now to FIGS. 5A–5F, various cut patterns for forming the tip 14 are shown. In its simplest form, the jaws 40, flexural members 48 and outer tubular housing 19 of the tip 14 are formed from a single capped tubular element. The foregoing components are formed by laser cutting or otherwise cutting or etching the tubular blank in a patterned fashion such as those illustrated in FIGS. 5A–F. Alternatively, the jaws and tubular housing 19 can be formed by a stamping operation such as that known as deep drawing.

A stopping edge 46 is formed on the proximal end of each jaw member 40. The stopping edge 46 may be arcuate, as shown in FIG. 5A; however, as will be recognized by one of skill in the art, the stopping edge 46 can also have many other geometries. For instance, a properly located straight circumferential cut will also limit the fully opened angle of the jaw members 40.

The removal of material or other forming technique which results in the stopping edge contour provides the necessary clearance for the jaw member 40 to rotate relative to the tabs 44. The proximal extremity of the illustrated stopping edge 46 forms, in part, the tabs 44 when bent inward. Moreover, as a function of their geometry, the stopping edges 46 limit the range of motion possible for each associated jaw member 40. As illustrated in the embodiment of FIG. 2, the jaws have a maximum opening angle, α. When the stopping edge 46 bottoms out against the outer wall of the inner sleeve 16 or outer sleeve 18 the full range of motion for the jaw members has been traversed. In one embodiment, the maximum angle, α, is about 120°. In other embodiments, α can range from about 60° to about 130°.

Any of a variety of alternative structures can be used to limit arcuate travel of the jaws, such as a pin or folded tab on one of the actuator shaft 16 (or collection chamber) or outer sleeve 18 which slides within a complementary slot on the other of the shaft 16 or sleeve 18. In one embodiment, the outer sleeve 18 in the area of tip 14 is provided with one or two or more generally U-shaped cuts, with the parallel legs of the U preferably extending in the axial direction. The cuts may be made such as by laser cutting, etching, stamping, or other known technique. The material at the center of the U-shaped cut may be folded radially inwardly to produce a tab, which may extend through the distal portion 30 of actuator shaft 16 in between a proximal and distal edge such as may be formed on either side of a complementary opening. The distance in the axial direction between the proximal and distal edge will produce a limit on the axial travel of the outer sleeve 18 with respect to the actuator shaft 16. This will in turn produce a limit on the range of motion of the jaws as will be apparent to those of skill in the art in view of the disclosure herein. The resulting hard stops in the range of axial motion between the inner and outer tubes prevents over opening and over forceful closing of the jaws, which could result in damage to the pivot pins or other undesired consequences.

The stopping edges 46 also cooperate with axial cuts 50 to isolate a pair of flexural members 48 as the only structural connection between the jaw members 40 and the cutter tip housing 19 (which may be the distal portion of the outer sleeve 18 in a rigid body embodiment). The flexural members 48, therefore, are the flexible linkage between the jaw members 40 and the cutter tip housing 19 which allow the jaw members 40 to open and close relative to each other. A springy quality of the flexural members 48 tends to hold the jaw members 40 in a normally closed or semi-closed position; however, as will be recognized by one of skill in the art, the jaw members 40 can alternatively be configured to be biased in a normally open position.

When the inner actuator shaft 16 is moved distally relative to the outer sleeve 18, the tabs 44 are advanced distally along an axial path. The flexural members 48 prevent distal movement of an outside portion of the jaw member 40 and thereby a rotational opening moment is set up with the tip 14. The tip 14 is, therefore, forced open. As will be appreciated, a corresponding proximal movement of the tabs 44 relative to the remainder of the tip housing 19 creates a closing moment. This basic translation of axial movement into lateral movement is used throughout the various applications of the articulating mechanism of the present invention, including, but not limited to, the biopsy device described in detail herein.

FIGS. 5A–5F illustrate different embodiments of the flexural members 48. In essence, the flexural members 48 are thin, axially extending strips of the material of cutter tip housing 19 which are coupled at a proximal end to the housing and at a distal end to the jaw member 40. The circumferential width of the flexural members 48 generally ranges from about 0.025" to about 0.035". Although each of FIGS. 5A–5F illustrates only a single flexural member 48 per jaw 40, two or more flexural members 48 per jaw 40 may also be provided. See, e.g. FIG. 19. While the illustrated embodiments utilize flexural members 48, as will be recognized by one of skill in the art, the flexural members could also be biased hinges, non-compressible straps, and the like.

In the illustrated embodiments, the flexural members 48, jaw members 40 and cutter tip housing 19 are advantageously formed from a single tubular member. Each flexural member 48 is preferably formed between two bilaterally symmetrical longitudinal cuts 50 of a desired length. The cuts 50 begin at a point proximal to the distal end of the tip 14 and extend proximally. In one embodiment, the cuts begin between about 0.050" and about 0.060" from the distal end of the outer sleeve 18 and extend proximally for between about 0.180" and about 0.200". In other embodiments, the cuts extend proximally between about 0.150" and about 0.250".

Figure 5C:
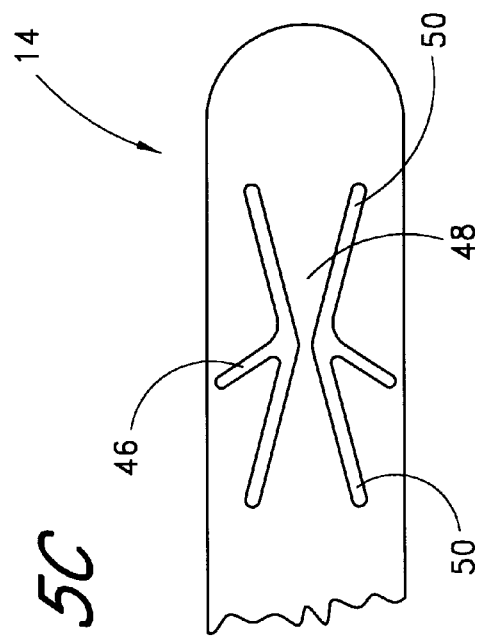
Figure 5F:
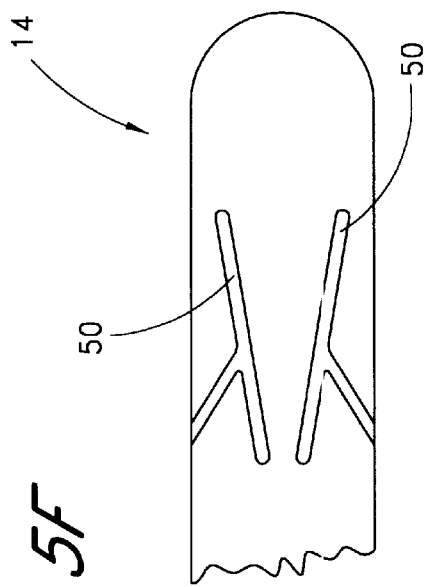
Figure 5D:
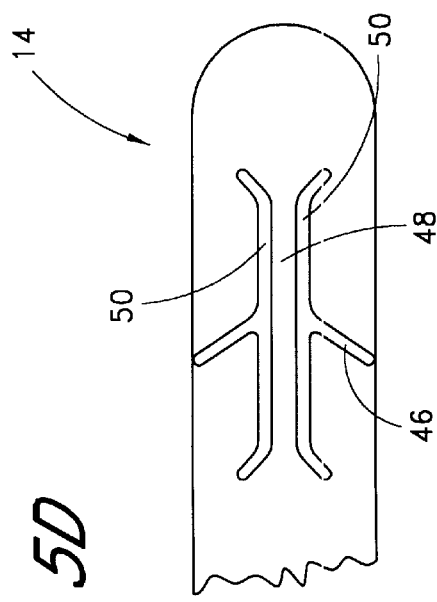
Figure 5E:
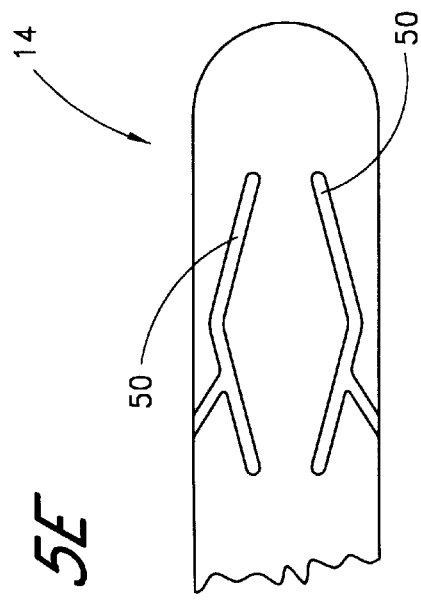

As illustrated, the mirror-image cuts 50 can be substantially linear in an axial direction (see FIG. 5A), crescent-shaped (see FIG. 5B) or variations on hour-glass shaped (see FIGS. 5C and 5D). The straight sides illustrated in FIG. 5A tend to create stress risers at the axial ends of the flexural member 48. The embodiments of FIGS. 5B–5D tend to more evenly distribute the bending stresses. Alternate shapes such as those shown in FIGS. 5E and 5F produce different effects on the flexure properties of the tip 14. The cuts 50 may conveniently be made by laser; however, various other forms of cutting, machining or molding are also contemplated.

By arranging the flexural members 48 circumferentially as far as possible from the tabs 44, maximum closing force can be achieved in the jaw members 40. In addition, this location results in the arrangement of the flexural member 48 being substantially centralized between the tabs in a symmetrical fashion. Thus, a torsional stability results from the illustrated design because the resultant moment (i.e., the result of the two counteracting moments) created by the flexural member 48 is reduced. In addition, the longitudinal placement of the cuts determines the longitudinal placement of the flexural member. As will be appreciated, the longitudinal placement of the flexural member 48 relative to the tabs 44 impacts the opening and closing moments discussed above.

In some embodiments, the single or multiple sample biopsy device 10 can be made from several different components. Because the jaw members 40, the flexural members 48, and the outer sleeve 18 are advantageously a unitary structure in the illustrated embodiment, they are preferably made from a material which is springy enough to provide the requisite flexing properties of the flexural members 48, rigid enough to function properly as the outer sleeve 18, and strong enough to withstand multiple sampling and the associated repeated flexing. Some presently preferred materials include, but are not limited to, stainless steel, and super elastic materials including nickel titanium alloys such as Nitinol. Other metals, or any of a wide variety of polymeric materials well known in the medical device art may also be used. Other embodiments are also envisioned in which a plurality of materials are combined to form different components of a single device.

Figure 7:
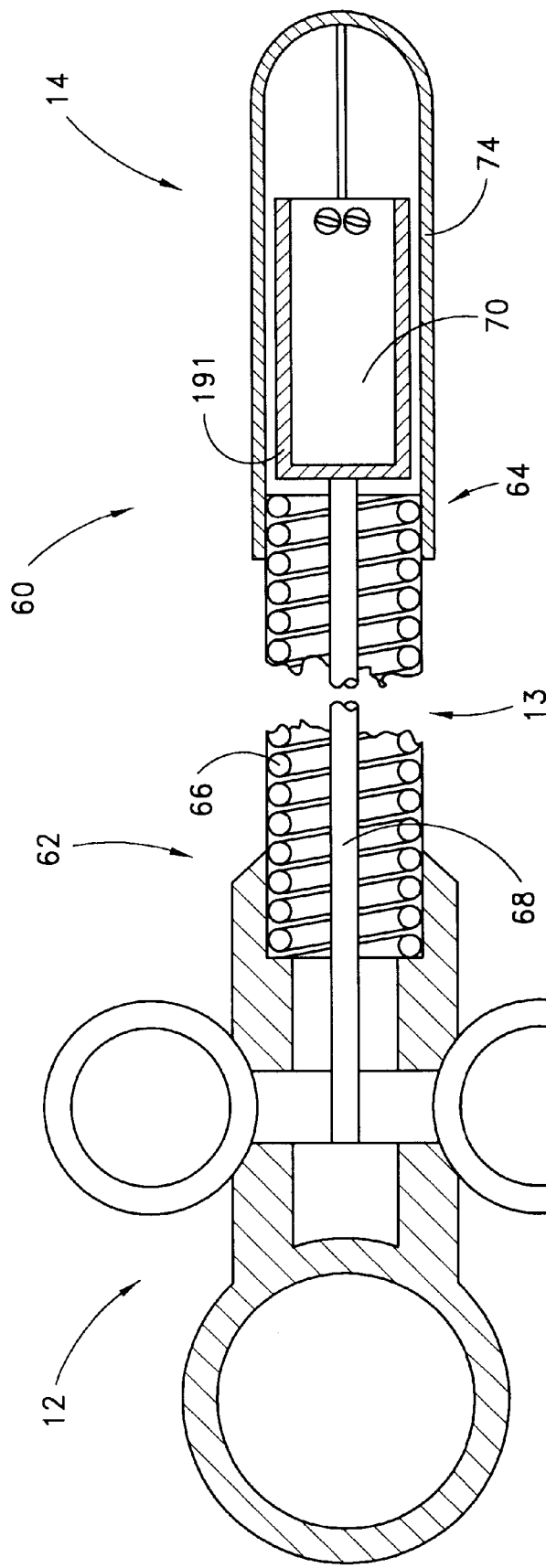
FIG. 7 is a cross-sectional side elevational view of a flexible shaft embodiment of the present invention.

Referring to FIG. 7, there is illustrated a flexible shaft biopsy device 60 in accordance with another aspect of the present invention. The flexible shaft biopsy device 60 generally comprises a proximal end 62, a distal end 64, and an elongate flexible body 13 extending therebetween. Proximal end 62 is provided with a control 12 as has been described. Distal end 64 is provided with a tip 14 such as any of those previously disclosed herein.

The elongate flexible tubular body 13 comprises a first element 66 and a second element 68, which are laterally flexible and axially reciprocally moveable with respect to each other to translate movement from the proximal control 12 to the tip 14. In the illustrated embodiment, the first element 66 comprises a flexible spring coil body as will be understood by those of skill in the flexible catheter arts. Depending upon the intended clinical application, the spring coil body may have an axial length within the range of from about 10 cm or less to as much as 300 cm or longer. The outside diameter may be optimized to suit the particular application, such as may be required by the inside diameter of the working channel or other introducer lumen through which the device 60 is to be inserted. In general, the outside diameter of the tubular body 66 will be no more than about 5 mm, and, preferably within the range of from about 1.8 mm to about 3.7 mm. The coil may comprise any of a variety of materials such as stainless steel, nitinol, or others known in the art. The wire may have a circular cross-section as illustrated, or rectangular, oval, or other cross-section depending upon the desired clinical performance.

The spring coil may be further provided with an outer and/or inner elastomeric sleeve such as an outer heat shrink tubing as is known in the art. In one embodiment, the heat shrink tubing comprises high density polyethylene having a wall thickness of about 0.002". Alternatively, an outer jacket may be provided on the spring coil body through any of a variety of techniques such as spraying, dipping, extrusion and the like. The flexible tubular body may alternatively comprise a thin walled metal such as hypodermic needle tubing, a polymeric extrusion, or other flexible structure.

The second element in the illustrated embodiment comprises an elongate actuator shaft in the form of a flexible pull/push wire 68. The cross-sectional configuration, diameter and material of the pull/push wire 68 is preferably selected to optimize the pulling and pushing characteristics necessary to impart sufficient cutting force or other opening or closing force to the tip 14. In one embodiment, a round cross-section stainless steel wire having a diameter of about 0.015" and an axial length of about 60" has been found useful. The wire may have a constant diameter throughout, or may be tapered or stepped down from a larger diameter at the proximal end to a smaller diameter at the distal end depending upon the desired flexibility characteristics of the device. In an over the wire embodiment, the pull wire 68 is provided with an elongate central guidewire lumen (not illustrated).

The distal end of the pull wire 68 is connected to a sample collection chamber 70. The sample collection chamber 70 comprises a generally cylindrical wall 191, axially movably disposed within the housing 74 of tip 14. The operation of the wall 191, outer housing 74 and cutting jaws on the tip 14 may be in accordance with embodiments previously disclosed herein.

In a flexible shaft embodiment, the overall flexibility and maneuverability of the biopsy tool will be limited by the axial length of the cutting tip. Thus, the cutting tip is preferably maintained at a relatively short axial length, such as no more than about 2 cm and, preferably, no more than about 1.0 or 1.5 cm long. The axial length of the cylindrical wall 191 which defines sample collection chamber 70 will normally be less than the overall length of the cutting tip.

The axial length of collection chamber 70 can be optimized in any particular embodiment, taking into account the desired volume for the collection chamber 70, as well as the maximum permissible length of the collection chamber 70 in view of the desired flexibility for any particular application. As with other embodiments herein, the designation "collection chamber" refers to a portion of the open central lumen proximal to the cutting edges of the jaws which is available for receiving samples. That central lumen may extend throughout the entire length of the shaft, or may terminate such as in embodiments where the interior actuating element comprises a solid rod or other nontubular structure along at least a portion of its axial length.

In a single or relatively few bite device, the jaws can be connected directly to the actuating member and there is no need for a collection chamber apart from the volume of the jaws. When the device is utilized for its open lumen, there is no discrete collection chamber structure but a continuous axially extending lumen throughout as will be appreciated by those of skill in the art in view of the disclosure herein. Thus, the collection chamber is the open area proximal to the cutting edges on the jaws, regardless of how it may be structurally contained.

Referring to FIG. 8, there is illustrated a further feature of the present invention, which may be adapted either to the rigid body or the flexible body embodiments of the multiple sample tissue biopsy device. In the illustrated embodiment, the actuator shaft 16 comprises an elongate tubular element such as a section of hypodermic tubing or polymeric extrusion in a relatively rigid embodiment, or an inner spring coil tubular element in a relatively flexible embodiment. In either construction, the actuator shaft contains a central lumen 69 such as for receiving an axially moveable core wire 71.

Figure 9:
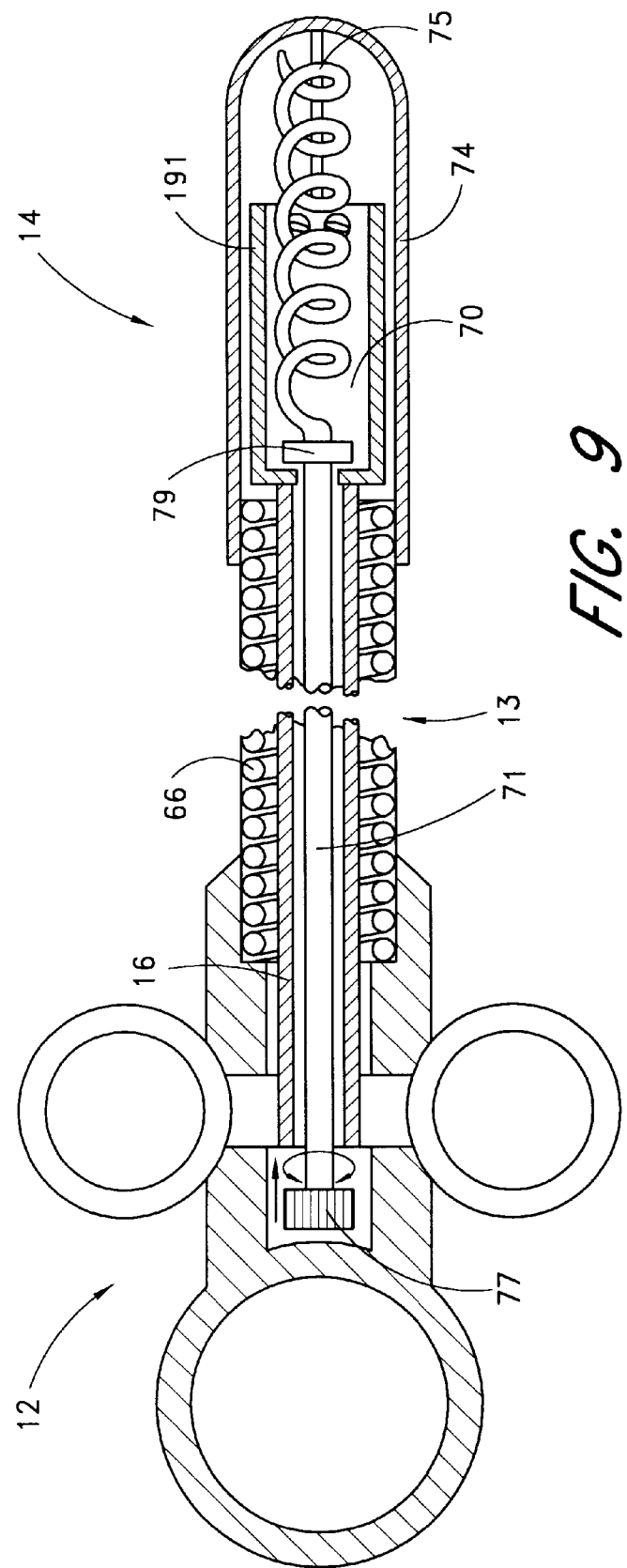
FIG. 9 is an embodiment like that of FIG. 8, with a tissue auger in the central lumen.

The core wire 71 in the embodiment of FIG. 8 accomplishes two functions, either one of which can be utilized without the other. For example, the core wire 71 is provided with a distal harpoon or needle tip 73 for skewering tissue samples which have been severed by the cutting tip 14. The harpoon tip 73 can be useful in helping maintain the sequential order of the samples, as well as controlling handling of the samples following removal from the patient. Modifications of the present embodiment include the use of an auger 75 as illustrated in FIG. 9, which may be rotated such as through the manual manipulation of an auger knob 77 at or about the proximal handle 12 to pull tissue within or expel tissue from the tissue collection chamber 70. Any of a variety of tissue augers and/or harpoons may be readily incorporated into the sample device of the present invention, such as those disclosed in U.S. Pat. No. 5,562,102 to Taylor, the disclosure of which is incorporated in its entirety herein by reference.

As an independent feature of the embodiment of FIG. 8, the core wire 71 is provided with a distal stop 79. As illustrated, the distal stop 79 resides at a proximal end of the sample collection chamber 70, and is axially movable within the cylindrical wall 72. Distal advancement of the core wire 71 causes the stop 79 to advance distally, thereby expelling the contents of the sample collection chamber 70. Distal advancement may be accomplished through any of a variety of structures at or about the handle 12, such as levers, slider switches, push button or the like. In the embodiment illustrated in FIG. 9, the auger knob 77 performs a dual function of rotation to advance tissue along the auger 75, as well as axial displacement to advance the auger 75 and stop 79 distally from the sample collection chamber 70.

Figure 10:
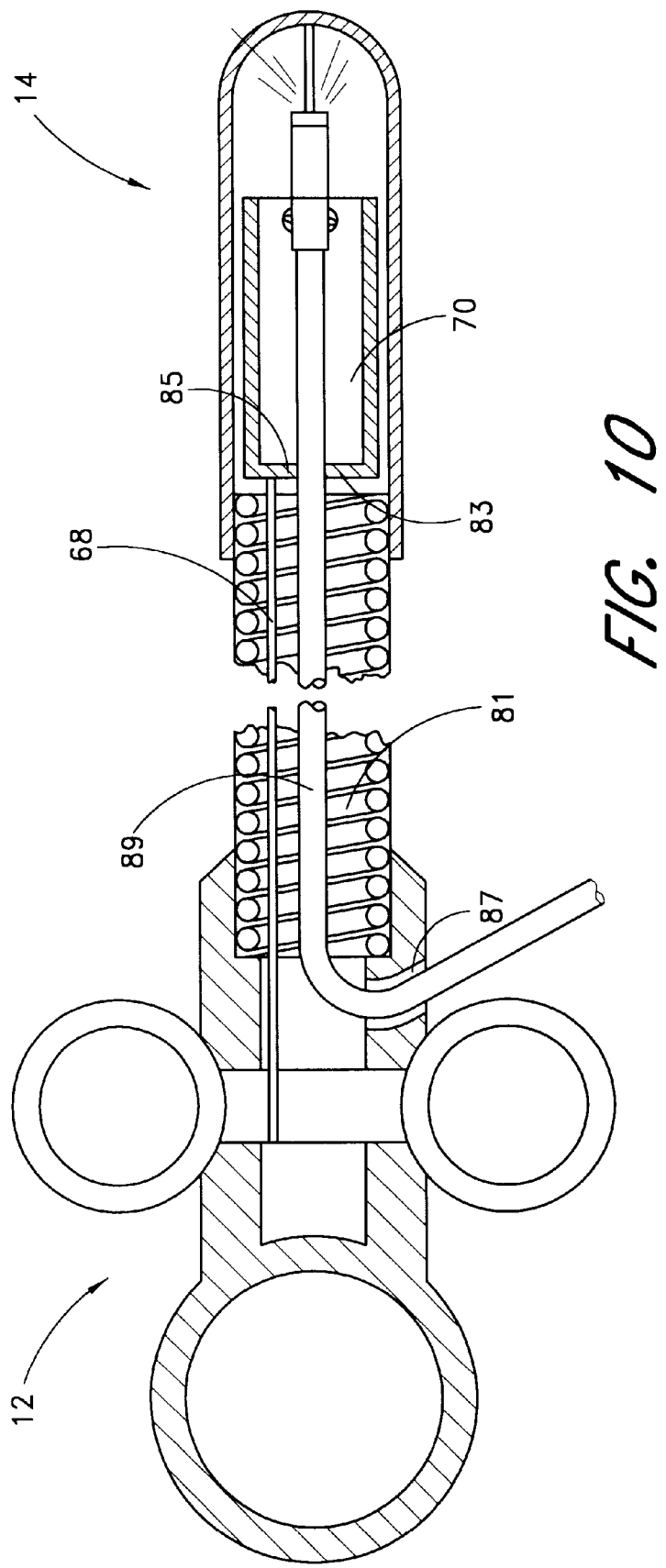
FIG. 10 is a cross-sectional side elevational view of an alternate flexible shaft embodiment of the present invention.

FIGS. 10 and 11 illustrate cross-sectional side elevational views of alternate embodiments of the present invention, adapted for accommodating structures and functions in addition to biopsy sampling. For example, referring to FIG. 10, the push/pull wire 68 in a flexible shaft embodiment is radially offset from the axial center of the shaft 13, thereby optimizing the cross-sectional area of an elongate central lumen 81 extending throughout the length of the flexible shaft 13. An aperture 83 is provided in the proximal wall 85 of the sample collection chamber 70, to provide communication between the sample collection chamber 70 and the central lumen 81. An access port 87 is provided on the proximal handle or manifold, so that an instrument 89 may be introduced through the access port 87, throughout the length of the central lumen 81, and into or beyond the sample collection chamber 70. In one embodiment, the lumen 81 is utilized to accommodate a fiber optic bundle to illuminate or visualize the working site. Any of a wide variety of alternative instruments may be advanced through the central lumen 81 as will be apparent to those of skill in the art in view of the disclosure herein.

In the relatively rigid shaft embodiment of FIG. 11, the elongate central lumen 81 which extends through the inner actuator element is provided with an open proximal end 91. The open proximal end 91 provides direct communication between the proximal end of the device and the distal end of the device, such as for the introduction of auxiliary instruments, sampling devices and the like. In addition, in either of the foregoing embodiments, the auxiliary lumen may be utilized for infusion of fluids with or without medication, as well as the aspiration of fluids. Biopsy samples may similarly be retracted throughout the length of the axial lumen if desired for a particular application.

FIGS. 14 through 18 illustrate features for incorporation into either of the flexible or rigid shaft embodiments disclosed above. Referring to FIG. 14, there is disclosed a front perspective view of a cutting tip 14 in an open orientation. The cutting tip 14 comprises a pair of jaws 40 each of which is formed from an axially extending support such as a generally half cylindrical portion 36 and a partial spherical cap portion 38. As with previous embodiments, alternate specific configurations for the jaws 40 can be used Mounting tabs 44 on the jaw 40 are positioned within one or more jaw mounting apertures 31 in or linked to the actuator shaft 16. Flexural members 48 are preferably intregally formed with the outer sleeve 18 and the jaw 40. Additional details and operation of the cutting tip 14 have been disclosed above.

Figure 15:
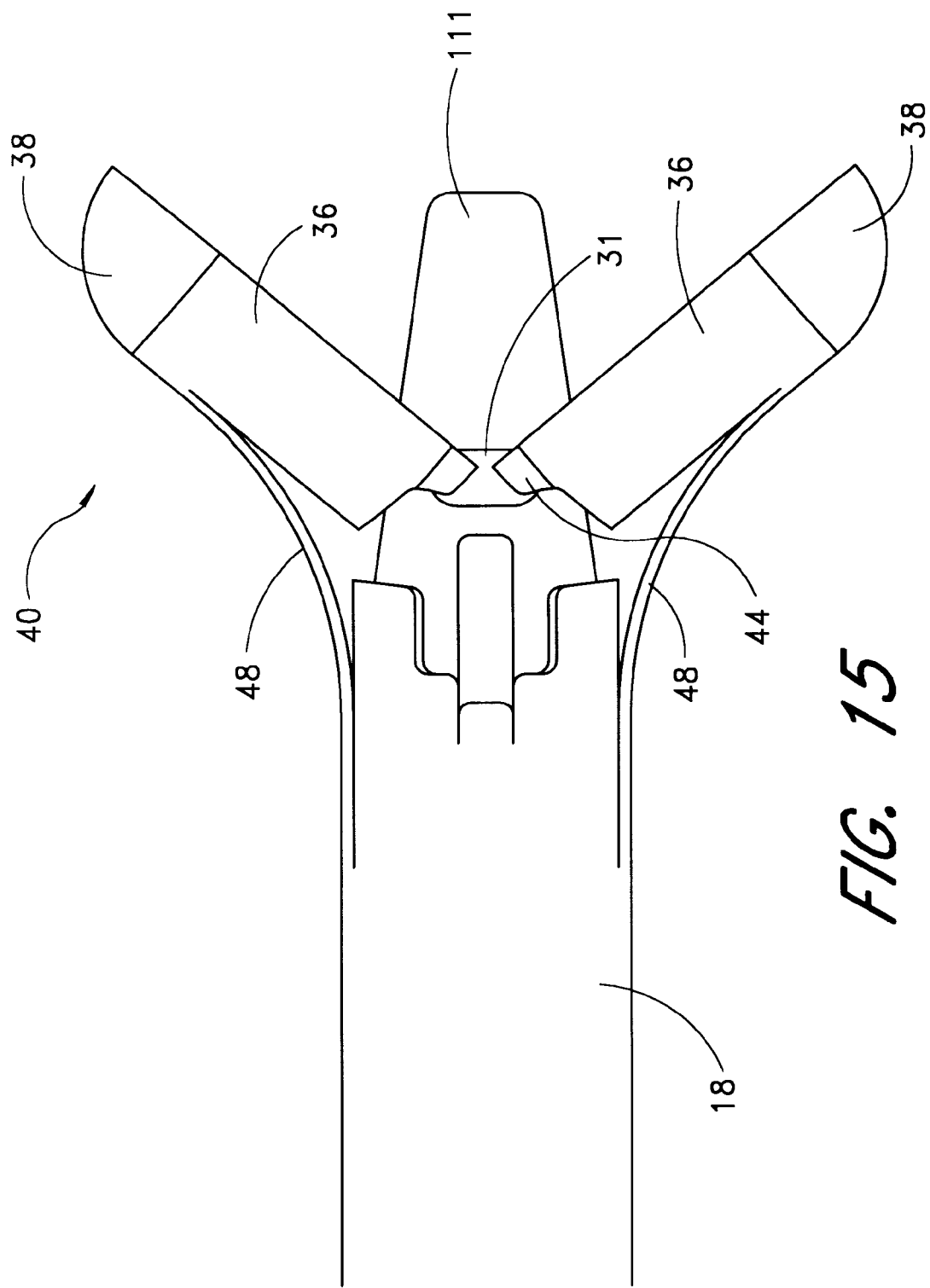
FIG. 15 is a side elevational view of the embodiment illustrated in FIG. 14.

In the embodiment of FIGS. 14 and 15, a pair of axially extending sample guide prongs 111 and 72 are disclosed. One or more axially extending prongs may be usefull in certain embodiments, such as where an oblique approach angle between the longitudinal axis of the cutting tip 14 and the tissue surface to be sampled is likely to be encountered. Axial prongs 111 and 72 assist in guiding the tissue sample into the sample collection chamber within the inner actuator 16.

As illustrated, the axial prongs 111 and 72 may be formed by removing opposing distal portions of the wall of a tubular element. Preferably, the axial prongs 111 and 72 are integrally formed as a distal extension of the inner tubular shaft 16, cylindrical wall 191 or analogous structure. The prongs 111 and 72 as illustrated each are provided with a sharpened distal end, which may be formed by inclining the radially inwardly facing surface of a distal portion of the prongs in a radially outward manner in the distal direction.

The guide prongs 111 and 72 may be either flat in transverse cross section, or curved such as when formed from a tubular component as illustrated In narrow prong embodiments, the arc length of each curved guide prong may range from as little as about 1 to 5 degrees (e.g., a sharp point) to 10 or 20 degrees around the circumference of the best fit circle on which the prong(s) reside. Narrow prong embodiments will generally have at least about two or three or four or more prongs. Prongs are preferably bilaterally symmetrically arranged around the longitudinal axis, and may be evenly circumferentially spaced about the longitudinal axis. Thus, for example, each prong or cluster of prongs may be spaced on centers of 180°, 120°, 90° and so on as will be apparent to one of skill in the art in view of the disclosure herein.

In wide prong embodiments, the prong can extend up to a full 360° circumferential width to form a cylindrical or other tubular shaped element. This design provided a coring tube which may have an annular sharpened distal edge, which may be enclosed within the jaws during placement and removal of the device. The coring tube as well as other embodiments may be proved with a serrated or saw toothed distal cutting edge, depending upon the intended use.

Intermediate prong widths, such as between about 20° and 180° often between about 35° and 90°, may also be used depending upon the intended use of the device. In the illustrated embodiment, a prong width of about 45° is shown. The foregoing prong width dimensions apply equally to prongs which are linear in the axial direction as illustrated in FIG. 14, and to prongs which are concave outwardly to otherwise curved or inclined in the axial direction such as those illustrated in FIG. 16.

The inner surfaces 113 of the prongs 111 and 72 may be smooth, or may be textured or provided with any of a variety of ridges or shapes for retaining samples. In one embodiment, the radially inwardly facing surface 113 is provided with a plurality of ratchet like ribs, which facilitate movement of tissue samples in a proximal direction, yet resist movement of tissue in a distal direction out of the central collection chamber.

Referring to FIG. 14A, there is disclosed a sample ejection feature of the invention, which can be incorporated into any of the devices disclosed herein. In the illustrated embodiment, the inner shaft 16 is provided with an axial slot or other opening 76, which, when the cutting tip 14 is in an open configuration, aligns with an axial slot 78 in the outer sleeve 18. One or more pairs of aligned openings such as axial slots 76 and 78 may be provided spaced circumferentially around the outer sleeve 18 as desired.

In use, following accumulation of one or a series of samples within the sample collection lumen of inner shaft 16, the cutting tip 14 is removed from the patient and opened as illustrated in FIGS. 14 and 14a. The sample ejection slots 76 and 78 are aligned such that a sample ejection tool (not illustrated) can be extended through the slots 76 and 78 and used to slide the tissue samples distally out of the biopsy device. In general, any of a variety of devices small enough to fit through the axial slots 76 and 78 may be utilized to assist in distal ejection of the tissue samples, such as tweezers, forceps, hemostats, pins or the like. Although a single sample ejection slot may be utilized, a pair of opposing sample ejection slots positioned approximately 180° apart around the periphery of the outer sleeve 18 may also be utilized. Three sample ejection slots may alternatively be used, and may be positioned at equal distances (e.g. 120°) around the circumference of the outer sleeve 18. Additional slots may also be used.

Figure 16:
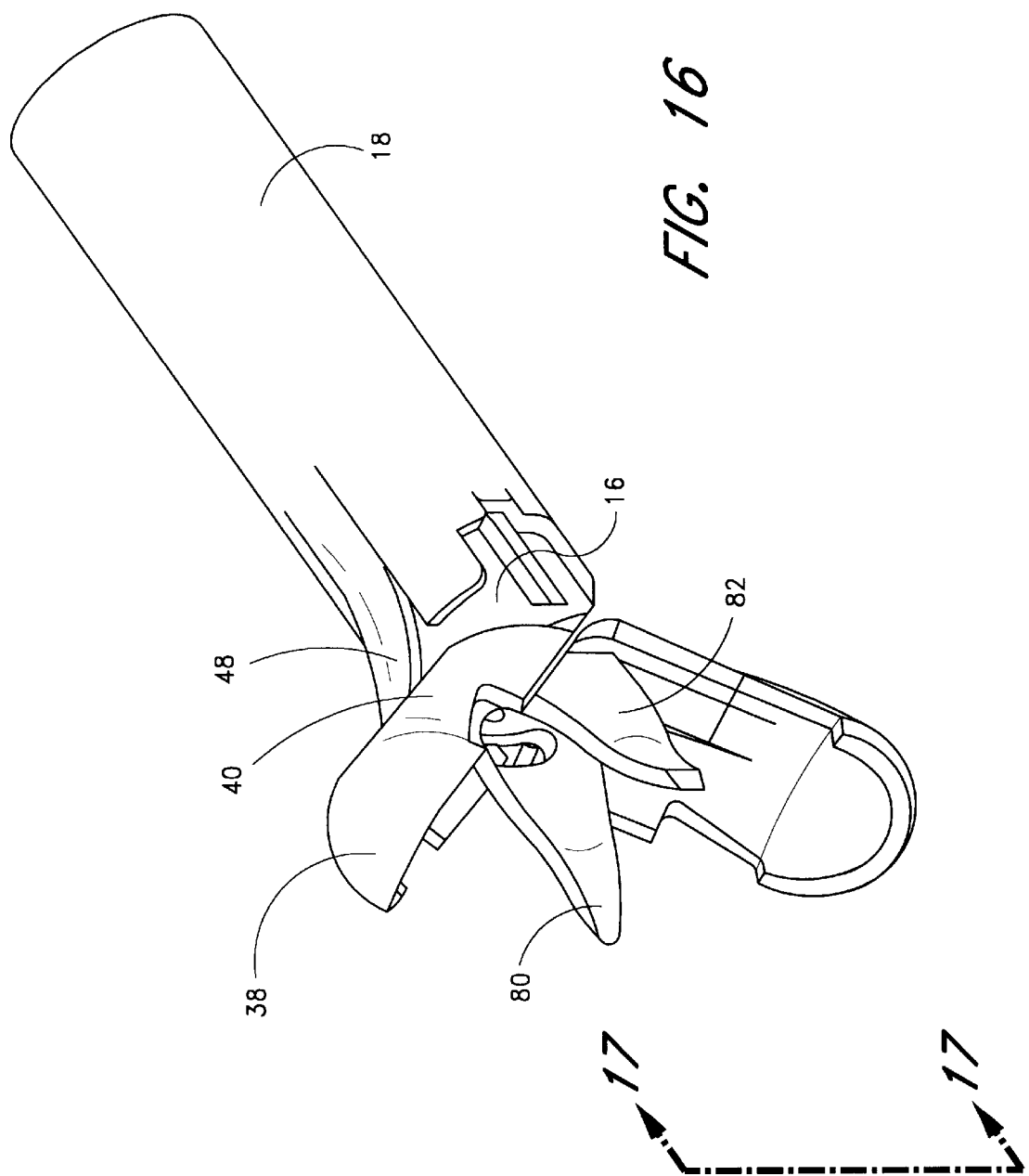
FIG. 16 is a front perspective view of a cutting tip having an alternate sample guide prong design.
Figure 17:
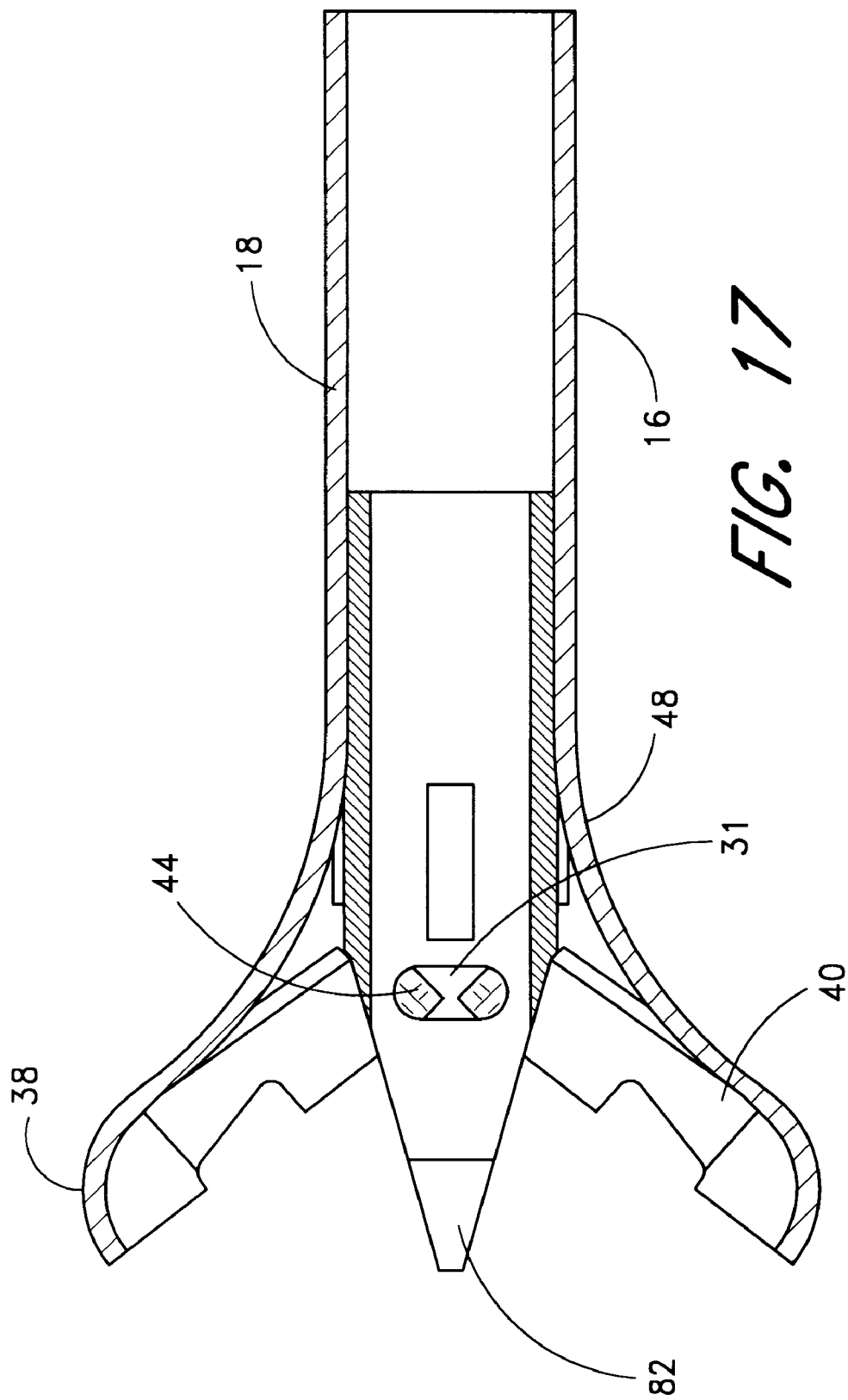
FIG. 17 is a cross sectional view taken along the lines 17—17 in FIG. 16.
Figure 18:
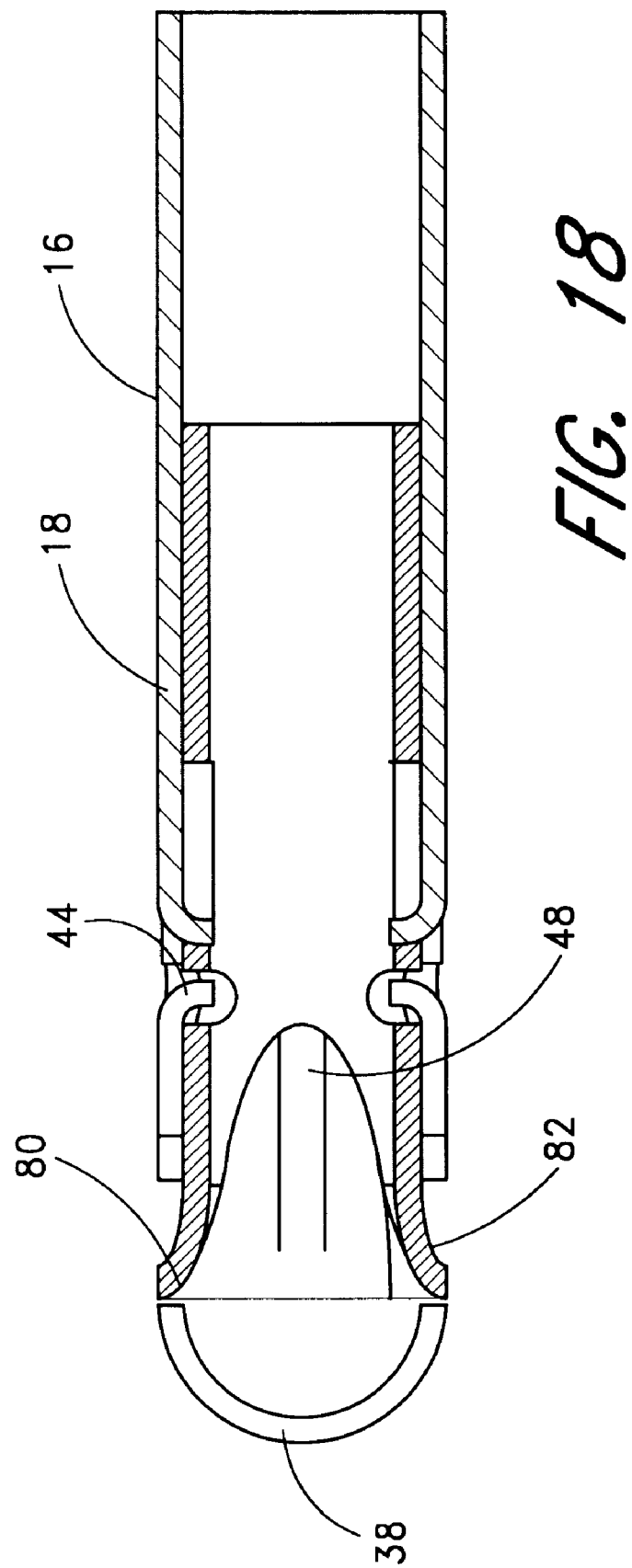
FIG. 18 is a cross section of the embodiment illustrated in FIG. 17, rotated 90° about its longitudinal axis and with the jaws in the closed orientation.

Referring to FIGS. 16 through 18, there is disclosed an alternate embodiment of the biopsy device, including modified sample prongs 80 and 82. In this embodiment, at least a distal portion of each of the prongs 80 and 82 inclines or flares radially outwardly in the distal direction. As can be seen from the cross sectional view of FIG. 18, the extent of the radial outward incline is no greater than the cross sectional diameter of the cap portion 38, so that the biopsy device may be advanced to the desired tissue sampling site without damaging tissue along the way. The winged prong embodiment of FIGS. 16 through 18 may facilitate obtaining an adequate sample size, particularly when the biopsy device approaches the surface of the tissue to be sampled at an angle other than 90°. In such an oblique approach, one of the winged prongs 80 and 82 will contact the surface to be sampled, and further distal movement of the biopsy device will cause tissue to be routed into the sample collection area of the biopsy device. A mark or other reference indicium may be provided on the proximal handle, to enable the clinician to know the rotational orientation of the winged prongs 80 and 82. Even with a 90° approach angle to the target tissue, the winged or flared prong(s) 80 and 82 may optimize sample size by slightly compressing the sample to be obtained by the cutter tip 14.

A further aspect of the present invention, which may be incorporated onto any of the foregoing embodiments, is the use of more than two flexural members 48. Thus, while each of the embodiments discussed above included a single flexural member 48 per jaw 40, there may be applications where multiple flexural members 48 per jaw 40 are desirable. For example, in larger diameter devices (e.g. 7 mm or 15 mm or larger) such as may be useful for laparoscopic, gynecological and arthroscopic surgery applications, the stability of the jaws 40 may be improved by providing a pair or three or more flexural members 48 for each jaw 40. A wider flexural member 48 also improves stability of the jaw; however, due to the curvature of the flexural member 48, relatively wide flexural members 48 may interfere with the desired opening and closing properties of the device. Thus, two parallel flexural members 48 may be used to connect the outer sleeve 18 to each jaw. The pair of flexural members 48 connected to a single jaw 40 may be positioned directly adjacent each other, or may be spaced circumferentially apart around the circumference of the outer sleeve 18, up to a distance which provides the desired stability to the jaw 40 yet does not create too much resistance to the opening and closing operation of the cutting tip 14.

Figure 19:
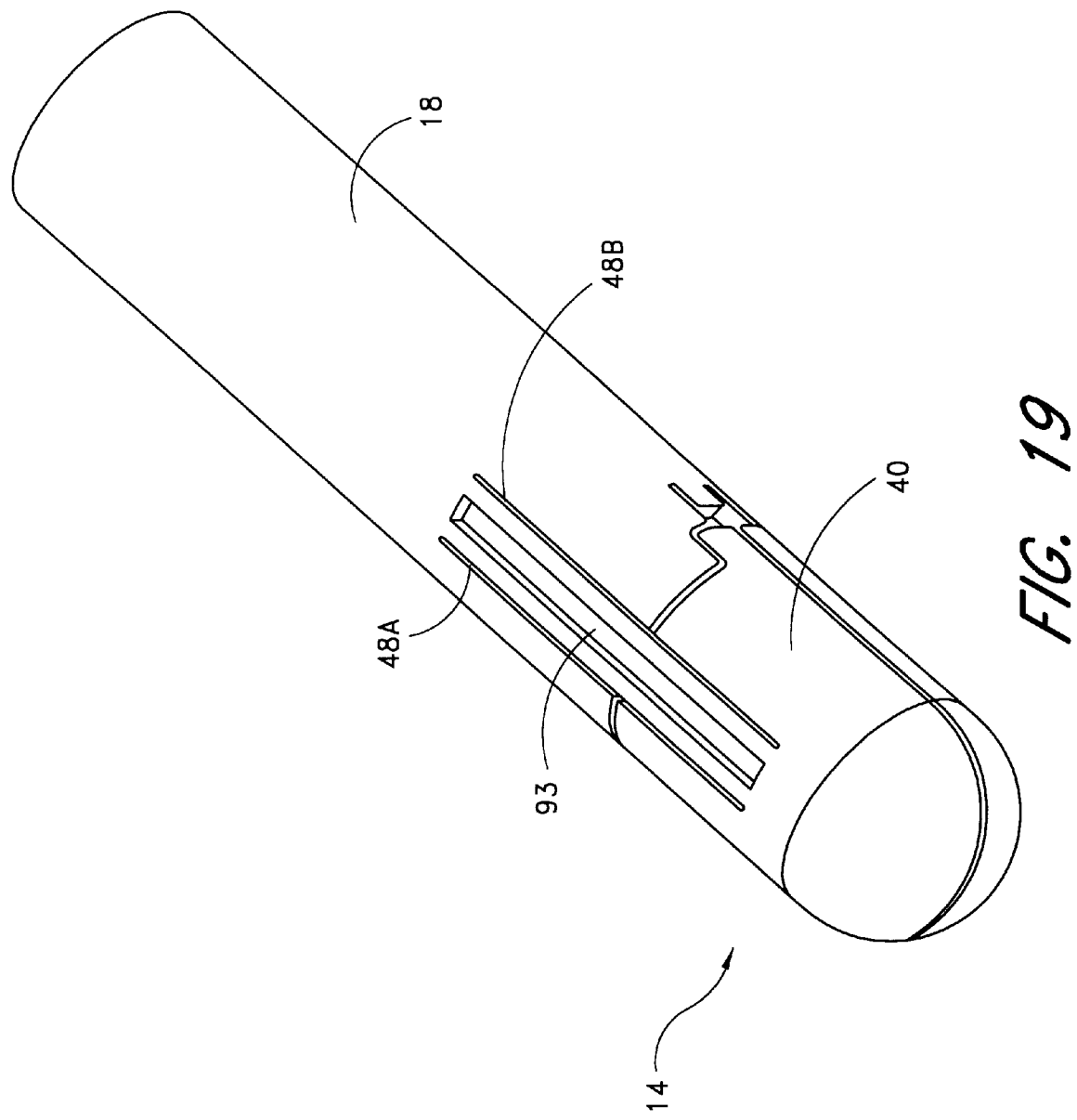
FIG. 19 is a perspective schematic view of a multiple flexure distal tip in accordance with the present invention.
Figure 20:
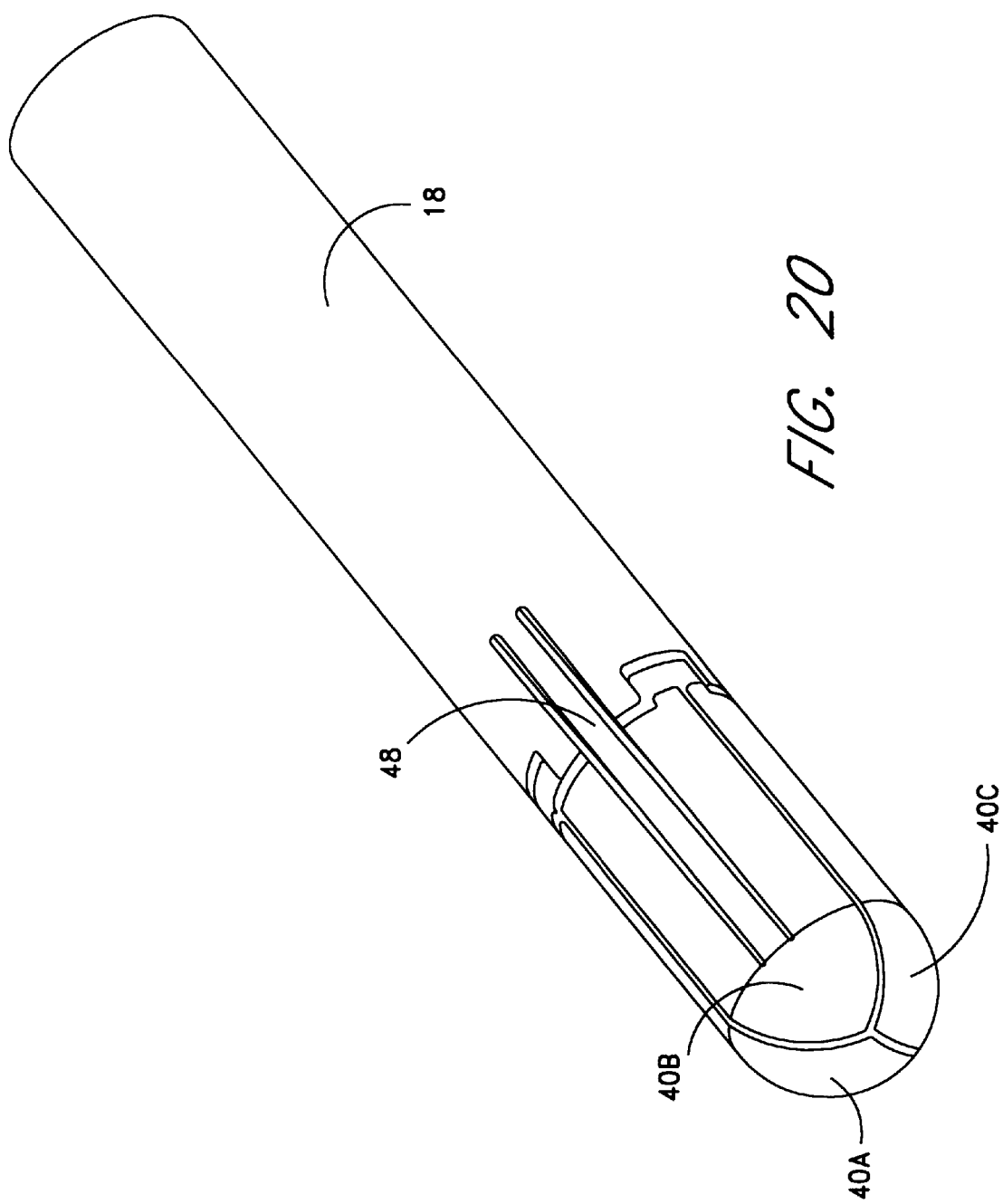
FIG. 20 is a perspective view of the distal tip of a three jaw embodiment of the present invention.

Thus, for example, FIG. 19 illustrates the distal end of a device in accordance with the present invention having first and second jaws 40. Each jaw is provided with first and second flexural members 48A and 48B, spaced apart by a width of a central axial slot 93. Two or more flexural members 48A and 48B per jaw 40 can readily be produced by providing multiple cuts in an axial direction as illustrated. Multiple flexural members 48A and 48B can be utilized to add additional control forces, column strength and stability.

Referring to FIGS. 20 through 23, there is illustrated the distal end of a device in accordance with the present invention having three jaws 40A, 40B and 40C. Each of the jaws 40A, 40B and 40C is provided with at least on flexural member 48 as has been discussed. Two or more flexural members 48 may also be utilized for each jaw 40A, 40B and 40C. Additional details of the embodiment of FIG. 20 will be readily apparent to those of skill in the art in view of the previous embodiments herein.

Figure 23:
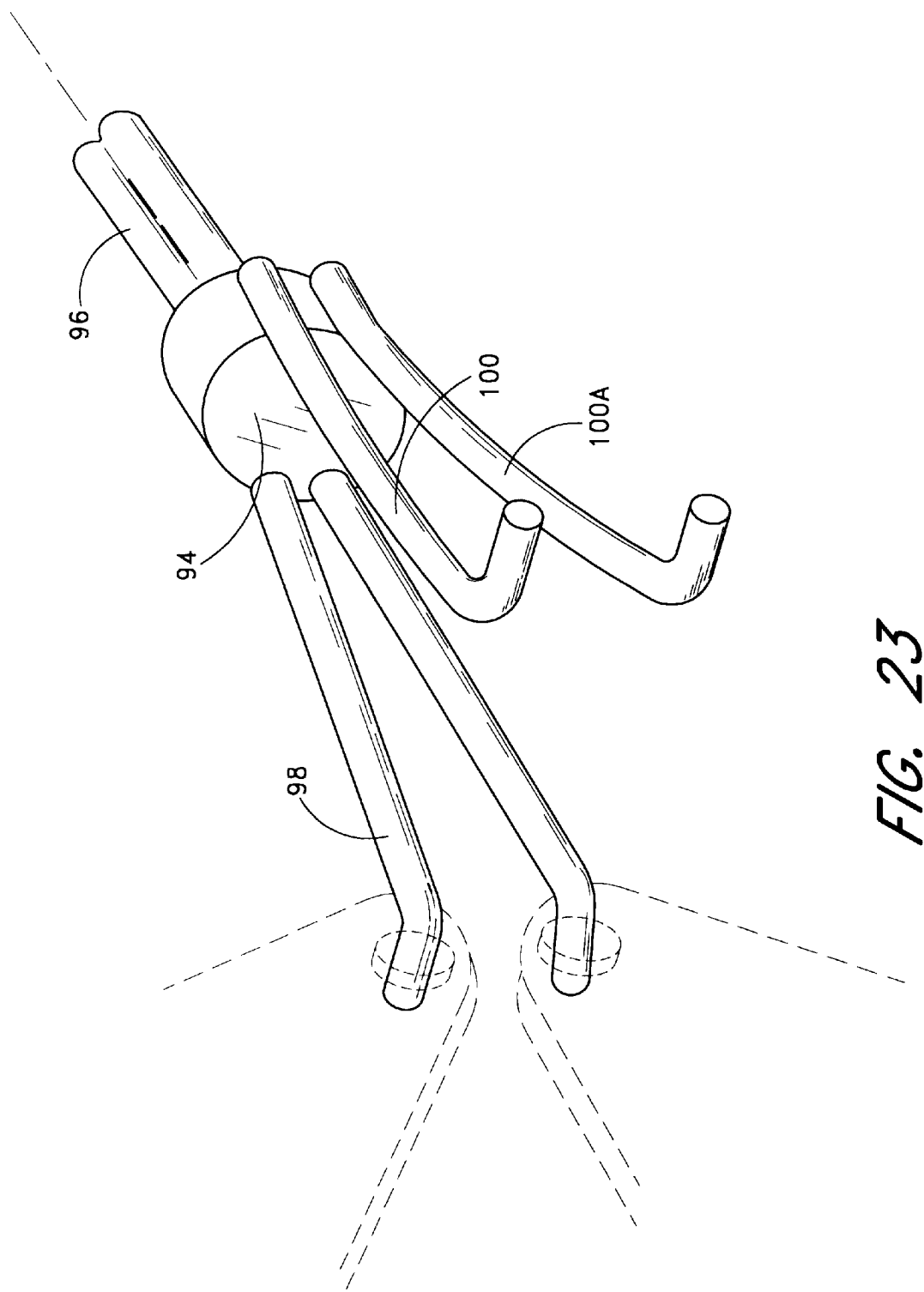
FIG. 23 is a perspective view of a wire actuator illustrated in FIGS. 21 and 22.

FIG. 21 illustrates a side elevational view of an embodiment in which a plurality of wires such as wires 90 and 92 are connected to the actuator 96 by way of a base 94. Alternatively, wires 90 and 92 can be directly connected to or integrally formed with the actuator 96. The distal ends 98 and 100 are pivotably connected to the jaw 40 to permit operation thereof as will be understood in view of previous disclosures herein. FIG. 22 illustrates a cross section through the device illustrated in FIG. 21, but rotated 90° around the longitudinal axis of the device. Thus, a first wire 100 is pivotably connected to the upper jaw 40 and a second wire 100A is pivotably connected to the lower jaw 40. FIG. 23 shows an enlargement of one actuator assembly as in FIGS. 21 and 22.

Figure 24:
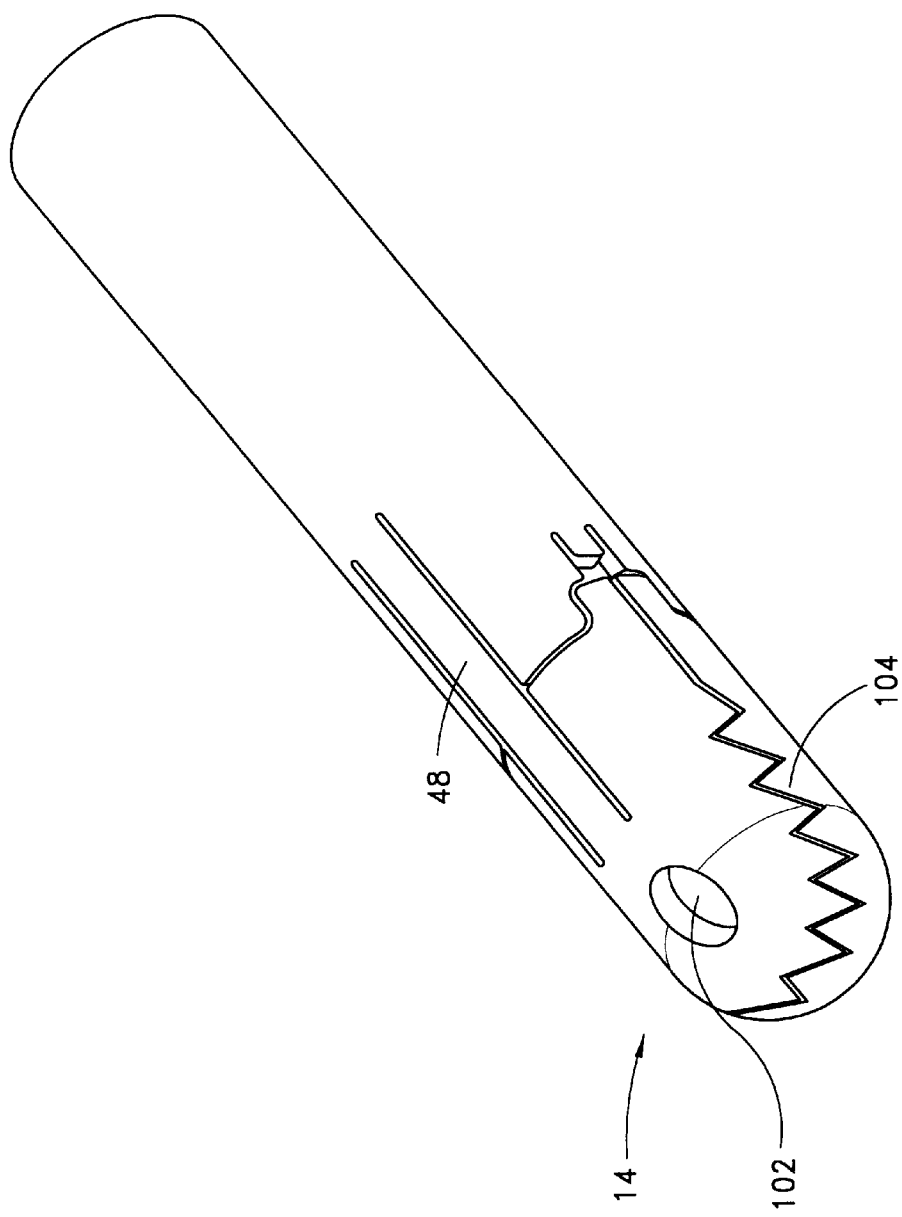
FIG. 24 is a perspective view of an alternate distal tip in accordance with the present invention.

Referring to FIG. 24 there is illustrated a partial schematic view of the distal end of a device in accordance with the present invention having features which can be substituted separately or in combination onto any of the previous embodiments. In particular, the device is provided with one or more fenestrations or apertures 102 for permitting fluid flow therethrough. Apertures 102 may be positioned at any of a variety of locations along the medical device, such as at or near the distal end as illustrated. Independently of apertures 102, the opposing jaws may be provided with complementary nonlinear surfaces such as a plurality of teeth or serrations 104. Teeth 104 of various shapes for puncturing or grasping tissue can be readily formed by modifying the laser or machining a path while making the cut.

While the present invention has been described primarily in the context of embodiments of a multiple sample biopsy device 10, it is contemplated that aspects and advantages of the inventive configuration of the present articulated mechanism can also find utility in other use environments. For instance, but without limitation, the same concepts can be utilized when forming single bite forceps or other articulating tools, such as biting forceps, electrodes, graspers, cutters, dilators, expanders, dissectors as well as other tissue manipulating devices, for example. The inventive configuration results in lowered production costs and ease of manufacturing and assembly in an articulated mechanism for converting axial motion of a first component relative to a second component into a radially outwardly directed or radially inwardly directed force.

For example, referring to FIG. 25 there is illustrated a perspective view of the distal tip of a medical device 106 incorporating the articulated mechanism of the present invention in the context of a nonbiopsy device. The device 106 comprises a distal tip 14 having a first and second blunt paddles 108, 110 such as forceps, graspers or dilators as will be appreciated by those of skill in the art. Each of the paddles 108, 110 is pivotably connected to an outer tubular body 18 in accordance with structures previously disclosed herein. One or more integral flexural members 48 is provided for each of paddles 108 and 110, to permit lateral movement of the paddles 108 and 110 as has been discussed previously herein. Paddles 108 and 110 can be replaced by any of a variety of structures, depending upon the intended application of the articulated mechanism of the present invention.

In addition, the inventive configuration opens the throat region 20 (also identified as lumen 81 in FIGS. 10 and 11) by removing any previously necessary pins or coupling structures which occluded the throat region 20. The open throat 20 can be utilized to pass any of a variety of instrumentation axially through the device, such as video, spectroscopy, and/or illumination devices, as well as diagnostic sensors (e.g. temperature, pressure, oxygen or $CO^2$). The central throat 20 may also accommodate therapeutic devices such as lasers, ablation or cautery devices and needles for fluid delivery, aspiration or biopsy. Central throat 20 may also be used as a suction or irrigation channel or as a medication delivery lumen. Depending upon the intended use of the device incorporating the articulated mechanism of the present invention, the open throat 20 may also house mechanical devices such as grinding burrs, augers, or tissue and bone masticators. Further uses of the present invention will be apparent to those of skill in the art in view of the foregoing disclosure.

In the context of a biopsy device, the sample collection chamber (e.g. central lumen) could be limited to the distal end or extended through the entire device. An embodiment in which the sample collection chamber extends throughout the length of the device enables insertion of another tool or media from, for instance, the control handle end of the device 10. For example but without limitation, a light fiber, fiber optic for visualization, a guide wire, saline, drugs or other media may be introduced through the central lumen. Moreover, an open lumen extending throughout the length of the device to the control end would allow the removal of tissue, debris, blood, or the like by a use of vacuum. The application of suction can also be used to aid the intake of samples during a biopsy procedure. Suction can be applied in a number of manners well known to those of skill in the art. For instance, wall suction in the operating room may be connected to the device or the device may be fitted with a simple plunger which will create a vacuum as the plunger is withdrawn either incrementally or steadily through the lumen 22.

A removable tissue collection container or axially moveable plunger could also be incorporated into the device to facilitate the orderly removal of multiple samples so as to not disturb their sequence. This orderly removal would allow better data collecting abilities because the tissue samples could be better tracked to their origin in the patient's body.

Although the invention has been described in terms of certain embodiments, other embodiments apparent to those of ordinary skill in the art also are within the scope of this invention. Thus, various changes and modifications may be made without departing from the spirit and scope of the invention. Accordingly, the scope of the invention is intended to be defined only by the claims that follow.

What is claimed is:

1. A tissue collection device, comprising:
   an elongate body, having a proximal end, a closed distal end, and an open inner lumen;
   a control on the proximal end of the body;
   a cutting tip on the distal end of the body, the cutting tip comprising a slit extending in a proximal direction from the closed distal end, the slit dividing the cutting tip into first and second opposing jaws integrally formed with the elongate body, the jaws being adapted to move between an open and a closed configuration;
   the jaws having an outside diameter delimiting an interior space when the jaws are in the closed configuration, the space being in communication with the open inner lumen; and
   at least one distally extending sample guide prong in the cutting tip, the at least one guide prong being contained within the outside diameter when the jaws are in the closed configuration.

2. A tissue collection device as in claim 1, wherein the body comprises an elongate flexible tubular body.

3. A tissue collection device as in claim 2, wherein the body comprises an elongate flexible tubular spring coil.

4. A tissue collection device as in claim 1, wherein the body comprises a relatively rigid tubular body.

5. A tissue collection device as in claim 1, wherein the body comprises an elongate tubular body, and further comprising an actuator element axially movably positioned within the tubular body and connected to the cutting tip, so that axial displacement of the actuator with respect to the tubular body causes the jaws to move between a closed position and an open position.

6. A tissue collection device as in claim 5, wherein the actuator comprises a solid rod.

7. A tissue collection device as in claim 5, wherein the actuator comprises a tubular element.

8. A tissue collection device as in claim 1, further comprising a sample collection chamber in a distal portion of the device.

9. A tissue collection device as in claim 8, wherein the sample collection chamber is defined within a tubular housing, said housing axially movably positioned within the cutting tip.

10. A tissue collection device as in claim 6, wherein the sample collection chamber further comprises a sample ejector.

11. A tissue collection device as in claim 10, wherein the sample ejector comprises an opening in the wall of the sample collection chamber.

12. A tissue collection device as in claim 1, wherein each of the first and second jaws is provided with a limit surface on a proximal portion thereof, for contacting the outer surface of the tip to limit opening of the jaws.

13. A tissue collection device as in claim 1, wherein the elongate body comprises a tubular housing, and each of the first and second opposing jaws is connected to the tubular housing by at least one flexural element.

14. A tissue collection device as in claim 13, wherein each of the first and second opposing jaws is connected to the tubular housing by at least two flexural elements.

15. A tissue collection device as in claim 1, wherein the guide prong comprises an annular distal edge.

16. A tissue collection device as in claim 1, comprising two bilaterally symmetrical guide prongs.

17. A tissue collection device as in claim 1, wherein the guide prong extends substantially linearly in the distal direction.

18. A tissue collection device as in claim 1, wherein the guide prong curves radially outwardly in the distal direction.

19. A method of obtaining multiple tissue samples, comprising the steps of:
   providing a sample collection device having an elongate body, a cutting tip on a closed distal end of the body, the cutting tip comprising a least one slit extending in a proximal direction from the closed distal end, the at least one slit dividing the cutting tip into at least two opposing jaws for isolating the samples from the surrounding tissue, and at least one distally extending sample guide prong;
   guiding a first tissue sample along the sample guide prong and into the jaws;
   closing the jaws to isolate the first tissue sample;
   opening the jaws;
   advancing a second tissue sample along the sample guide prong and into the jaws; and
   closing the jaws to isolate the second tissue sample.

20. A cutter tip for mounting on the distal end of a biopsy device, the tip comprising:
   a tubular housing having a proximal end and a closable distal end, the distal end of the tubular housing axially bisected into first and second jaw portions by a proximally extending cut therethrough;
   at least one sample guide prong extending distally within the first and second jaws;
   a tubular sample collection container axially movably positioned within the housing; and
   a moveable connection between the tubular sample container and the first and second jaws such that axial displacement of the tubular sample collection container in a first direction causes the first and second jaws to move laterally away from each other, and axial displacement of the tubular sample container in a second axial direction causes the first and second jaws to advance medially towards each other.

21. A cutter tip as in claim 20, wherein each of the first and second jaws further comprises at least one flexural element extending between the tubular housing and the jaw.

22. A cutter tip as in claim 21, wherein the flexural member is integrally formed with the jaw and tubular housing.

23. A cutter tip as in claim 21, comprising two flexural elements on each jaw.

24. A cutter tip as in claim 20, wherein the sample guide prong is an integral extension of the wall of the sample container.

25. An articulating mechanism for use in a medical device, comprising:
   a tube having an inner lumen;
   an actuator, axially moveably positioned within the tube;
   at least one slit extending in a proximal direction from a closed distal end of the tube, the at least one slit delimiting at least two laterally pivotable elements, at least a portion of which are integrally connected to the tube;
   the pivotable elements adapted to move into at least an open and a closed configuration; and
   the pivotable elements delimiting an interior space when they are in the closed configuration, the space being in communication with the inner lumen;
   wherein axial movement of the actuator with respect to the tube causes lateral movement of the pivotable elements.

26. A mechanism as in claim 25, comprising two laterally pivotable elements.

27. A mechanism as in claim 26, wherein the laterally pivotable elements are biopsy jaws.

28. A tissue collection device, comprising:
an elongate body, having a proximal end and a distal end;
a control on the proximal end of the body;
a cutting tip on the distal end of the body, the tip comprising first and second opposing jaws;
at least one distally extending sample guide prong in the cutting tip, and
a sample collection chamber in a distal portion of the device, the sample collection chamber defined within a tubular housing, said housing axially movably positioned within the cutting tip.

29. A tissue collection device as in claim 28, wherein the body comprises an elongate flexible tubular body.

30. A tissue collection device as in claim 29, wherein the body comprises an elongate flexible tubular spring coil.

31. A tissue collection device as in claim 28, wherein the body comprises a relatively rigid tubular body.

32. A tissue collection device as in claim 28, wherein the body comprises an elongate tubular body, and further comprising an actuator element axially movably positioned within the tubular body and connected to the cutting tip, so that axial displacement of the actuator with respect to the tubular body causes the jaws to move between a closed position and an open position.

33. A tissue collection device as in claim 31, wherein the actuator comprises a solid rod.

34. A tissue collection device as in claim 31, wherein the actuator comprises a tubular element.

35. A tissue collection device as in claim 28 wherein the sample collection chamber further comprises a sample ejector.

36. A tissue collection devices as in claim 35, wherein the sample ejector comprises an opening in the wall of the sample collection chamber.

37. A tissue collection device as in claim 28, wherein each of the first and second jaws is provided with a limit surface on a proximal portion thereof, for contacting the outer surface of the tip to limit opening of the jaws.

38. A tissue collection device as in claim 28, wherein each of the first and second opposing jaws is connected to the tubular housing by at least one flexural element.

39. A tissue collection device as in claim 38, wherein each of the first and second opposing jaws is connected to the tubular housing by at least two flexural elements.

40. A tissue collection device as in claim 28, wherein the guide prong comprises an annular distal edge.

41. A tissue collection device as in claim 28, comprising two bilaterally symmetrical guide prongs.

42. A tissue collection device as in claim 28, wherein the guide prong extends substantially linearly in the distal direction.

43. A tissue collection device as in claim 28, wherein the guide prong curves radially outwardly in the distal direction.

* * * * *